United States Patent
Heath et al.

(10) Patent No.: US 9,795,459 B2
(45) Date of Patent: *Oct. 24, 2017

(54) MEDICAL INSTRUMENT WITH MODIFIED MEMORY AND FLEXIBILITY PROPERTIES AND METHOD

(71) Applicant: D & S Dental, LLC, Johnson City, TN (US)

(72) Inventors: Derek E. Heath, Vero Beach, FL (US); Steven J. A. Treadway, Jonesborough, TN (US); Bobby J. Bennett, Johnson City, TN (US)

(73) Assignee: D & S Dental, LLC, Johnson City, TN (US)

( * ) Notice: Subject to any disclaimer, the term of this patent is extended or adjusted under 35 U.S.C. 154(b) by 166 days.

This patent is subject to a terminal disclaimer.

(21) Appl. No.: 14/538,416

(22) Filed: Nov. 11, 2014

(65) Prior Publication Data

US 2015/0164616 A1    Jun. 18, 2015

Related U.S. Application Data

(63) Continuation of application No. 13/396,034, filed on Feb. 14, 2012, now Pat. No. 8,911,573, which is a
(Continued)

(51) Int. Cl.
*C22F 1/10* (2006.01)
*A61C 5/02* (2006.01)
*C22F 1/00* (2006.01)
*C22F 1/08* (2006.01)
*C22F 1/18* (2006.01)
*C22C 19/03* (2006.01)
(Continued)

(52) U.S. Cl.
CPC .............. *A61C 5/023* (2013.01); *A61C 5/42* (2017.02); *C22C 19/03* (2013.01); *C22F 1/006* (2013.01); *C22F 1/008* (2013.01); *C22F 1/08* (2013.01); *C22F 1/10* (2013.01); *C22F 1/183* (2013.01); *A61C 2201/00* (2013.01); *A61C 2201/007* (2013.01); *C21D 1/26* (2013.01); *C21D 2201/01* (2013.01); *C21D 2201/02* (2013.01)

(58) Field of Classification Search
None
See application file for complete search history.

(56) References Cited

U.S. PATENT DOCUMENTS

| | | |
|---|---|---|
| 4,889,487 A | 12/1989 | Lovaas |
| 5,017,133 A | 5/1991 | Miura |

(Continued)

FOREIGN PATENT DOCUMENTS

| | | |
|---|---|---|
| WO | 0069359 | 11/2000 |
| WO | 2005070320 A1 | 8/2005 |
| WO | 2008098191 | 8/2008 |

*Primary Examiner* — George Wyszomierski
(74) *Attorney, Agent, or Firm* — Luedeka Neely Group, P.C.

(57) ABSTRACT

Medical instruments, particularly, endodontic instruments with unique limited memory characteristics, and methods for making such instruments. One embodiment includes heat treating a finished endodontic instrument. A related embodiment includes electropolishing a finished endodontic instrument and then heat treating the endodontic instrument.

7 Claims, 26 Drawing Sheets

Related U.S. Application Data continuation-in-part of application No. 12/950,536, filed on Nov. 19, 2010, now abandoned.

(60) Provisional application No. 61/263,192, filed on Nov. 20, 2009.

(51) Int. Cl.
*A61C 5/42* (2017.01)
*C21D 1/26* (2006.01)

(56) References Cited

U.S. PATENT DOCUMENTS

| | | | |
|---|---|---|---|
| 5,069,226 A | 12/1991 | Yamauchi et al. | |
| 5,102,333 A | 4/1992 | Suzuki et al. | |
| 5,137,446 A | 8/1992 | Yamauchi et al. | |
| 5,464,362 A | 11/1995 | Heath et al. | |
| 5,527,205 A | 6/1996 | Heath et al. | |
| 5,628,674 A | 5/1997 | Heath et al. | |
| 5,655,950 A | 8/1997 | Heath et al. | |
| 5,762,541 A | 6/1998 | Heath et al. | |
| 5,775,902 A | 7/1998 | Matsutani et al. | |
| 5,820,375 A | 10/1998 | Chalifoux | |
| 5,843,244 A | 12/1998 | Pelton et al. | |
| 5,879,160 A | 3/1999 | Ruddle | |
| 5,882,444 A | 3/1999 | Flomenblit et al. | |
| 5,941,760 A | 8/1999 | Heath et al. | |
| 6,042,376 A | 3/2000 | Cohen et al. | |
| 6,074,209 A * | 6/2000 | Johnson | A61O 5/025 433/102 |
| 6,149,501 A | 11/2000 | Farzin-Nia et al. | |
| 6,206,695 B1 | 3/2001 | Wong et al. | |
| 6,315,558 B1 | 11/2001 | Farzin-Nia et al. | |
| 6,410,886 B1 | 6/2002 | Julien | |
| 6,422,010 B1 | 7/2002 | Julien | |
| 6,431,863 B1 | 8/2002 | Sachdeva et al. | |
| 6,571,665 B2 | 6/2003 | Julien | |
| 6,579,092 B1 | 6/2003 | Senia et al. | |
| 6,593,010 B2 | 7/2003 | Izbicki et al. | |
| 6,783,438 B2 | 8/2004 | Aloise et al. | |
| 7,005,018 B2 | 2/2006 | Julien | |
| 7,018,205 B2 | 3/2006 | Abel | |
| 7,025,776 B1 | 4/2006 | Houser et al. | |
| 7,137,815 B2 | 11/2006 | Matsutani et al. | |
| 7,147,469 B2 | 12/2006 | Garman | |
| 7,779,542 B2 | 8/2010 | Aloise et al. | |
| 7,789,979 B2 | 9/2010 | Dooley et al. | |
| 8,062,033 B2 | 11/2011 | Luebke | |
| 8,562,341 B2 | 10/2013 | Luebke | |
| 8,727,773 B2 | 5/2014 | Luebke | |
| 8,911,573 B2 * | 12/2014 | Heath | A61O 5/023 148/563 |
| 2002/0137008 A1 | 9/2002 | McSpadden et al. | |
| 2004/0023186 A1 | 2/2004 | McSpadden | |
| 2004/0117001 A1 | 6/2004 | Pelton et al. | |
| 2005/0069837 A1 * | 3/2005 | Lewis | A61O 5/023 433/102 |
| 2006/0014480 A1 | 1/2006 | Aloise et al. | |
| 2006/0185169 A1 | 8/2006 | Lewis et al. | |
| 2007/0054238 A1 | 3/2007 | Hof et al. | |
| 2007/0137742 A1 | 6/2007 | Hao et al. | |
| 2007/0293939 A1 | 12/2007 | Shrivastava et al. | |
| 2008/0032260 A1 | 2/2008 | Luebke | |
| 2009/0130638 A1 | 5/2009 | Hof et al. | |
| 2010/0233648 A1 | 9/2010 | McSpadden et al. | |
| 2013/0269841 A1 | 10/2013 | Heath et al. | |

* cited by examiner

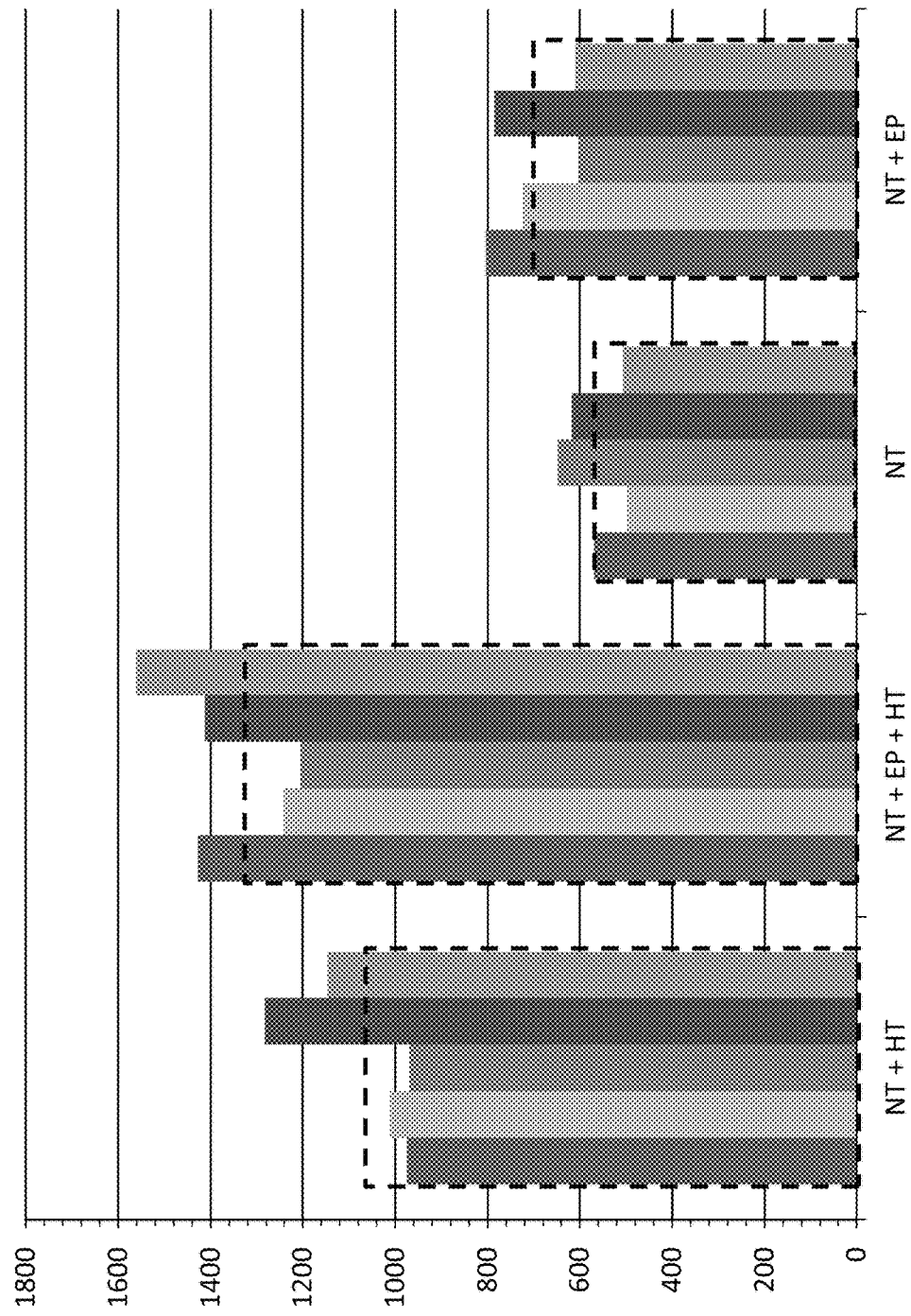

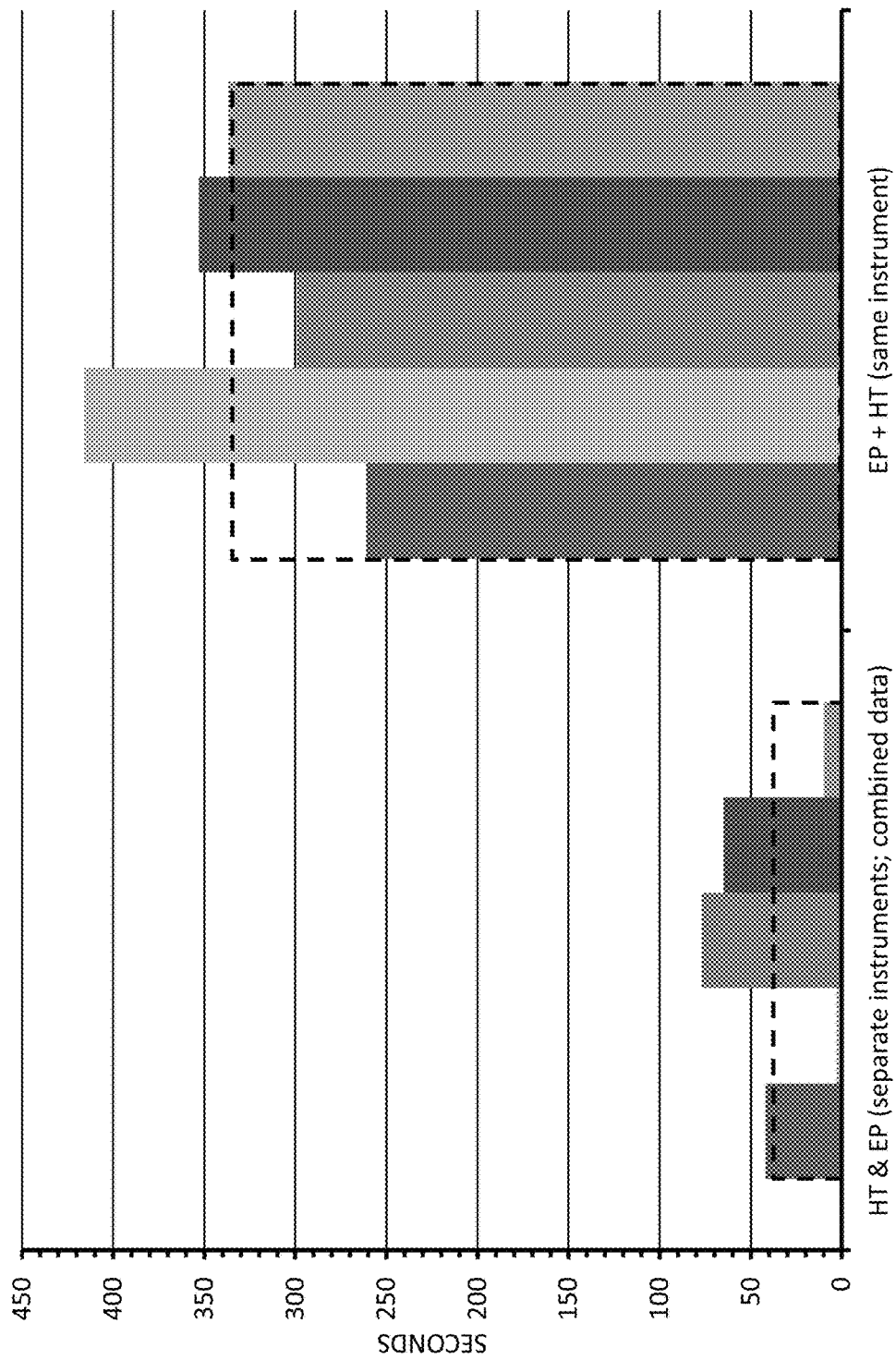

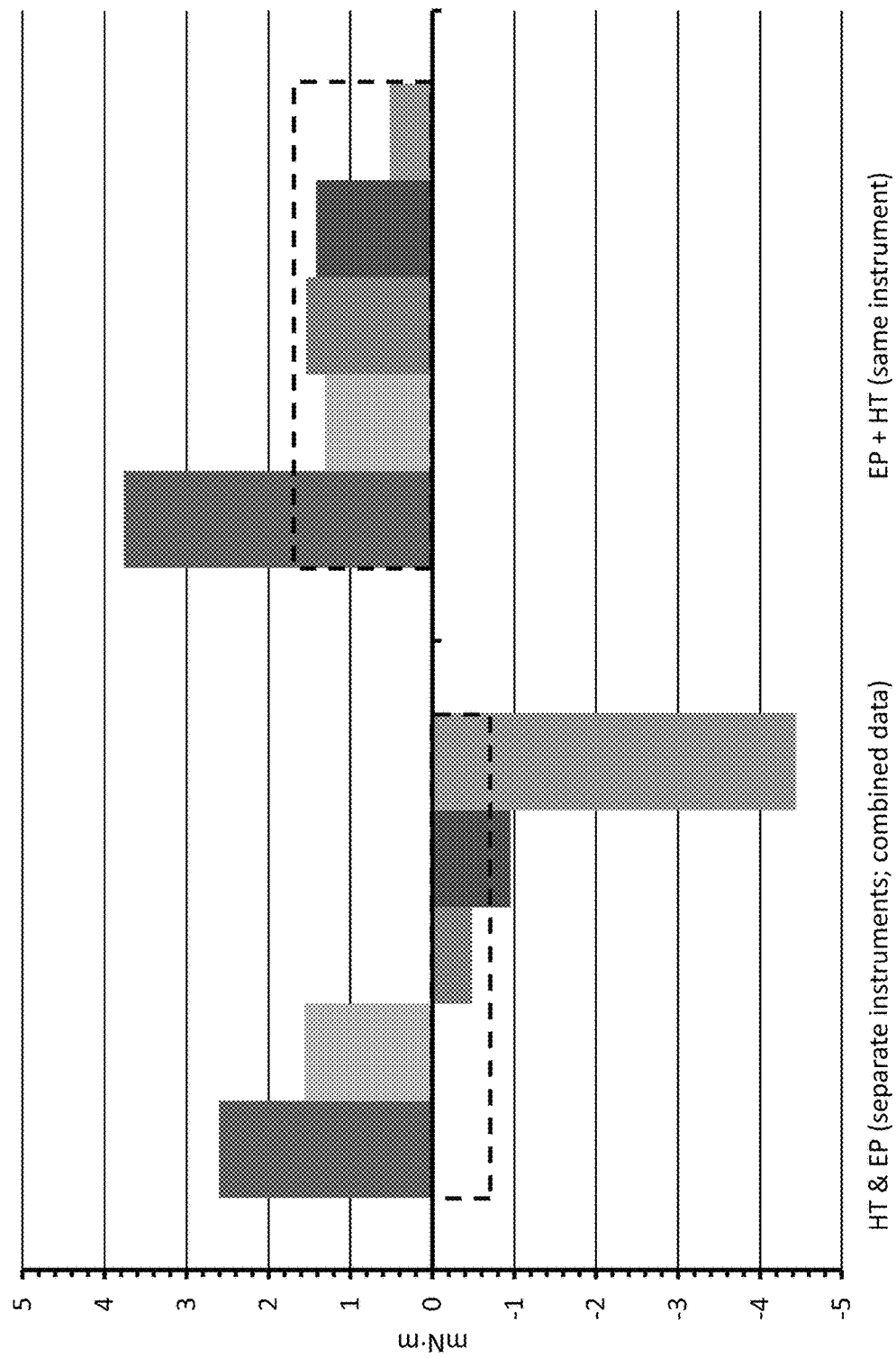

Angular Deflection

MEDICAL INSTRUMENT WITH MODIFIED MEMORY AND FLEXIBILITY PROPERTIES AND METHOD

CROSS-REFERENCE(S) TO RELATED APPLICATION(S)

This application is a continuation application of application Ser. No. 13/396,034, filed Feb. 14, 2012, now U.S. Pat. No. 8,911,573, which is a continuation-in-part application of application Ser. No. 12/950,536 filed Nov. 19, 2010, now abandoned, which claimed priority to provisional application Ser. No. 61/263,192, filed on Nov. 20, 2009, all of which are hereby incorporated by reference in their entirety.

FIELD

This disclosure relates to the field of medical instruments, manufacturing treatments, and methods of use therefor. More particularly, this disclosure relates to medical instruments and methods for manufacturing and using such instruments to provide medical instruments and techniques with unique desired properties.

BACKGROUND

The present disclosure relates to endodontic instruments, orthodontic instruments, other medical instruments, and to methods of making such instruments. Prior related medical instruments have been plagued with recurrent problems including, but not limited to, undesired lateral transportation in curved canals, difficulties with enlarging curvilinear canals while substantially maintaining the original center axis of the canals, and problems with binding and/or "screwing in" of prior NiTi instruments in such canals during endodontic or orthodontic procedures. For these and other medical procedures, there is a need for handheld probing, actuating, and/or surgical-type instruments with specific metallurgical and behavioral properties.

SUMMARY

The above and other needs are met by a method for modifying a physical characteristic of a medical instrument. The method comprises the steps of placing a medical instrument (e.g., an endodontic instrument) in a heated environment having a temperature of from about 450° C. to about 550° C. for from about 90 minutes to about 300 minutes, wherein the medical instrument is made from at least about 50% by mass of a superelastic alloy. Preferably, the endodontic instrument comprises a tapered endodontic instrument made of a nickel-titanium composition and configured as a file, rasp, broach, or other device for cleaning, scraping, extirpating, and/or debriding a root canal of a tooth. In one embodiment, the instrument is placed in the heated environment for a period from about 120 minutes to about 150 minutes. In a related embodiment, the instrument is placed in the heated environment for a period from about 180 minutes to about 300 minutes. In one embodiment, the placing step further comprises placing the endodontic instrument in a heated gaseous environment having a gas temperature of from about 490° C. to about 510° C. wherein the gaseous environment preferably is ambient air.

Preferably, the instrument undergoes a machining step to form a working portion prior to placing the endodontic instrument in the heated environment.

In one embodiment, the method for modifying a physical characteristic of an endodontic instrument described above is made by further including a step of electropolishing the endodontic instrument prior to placing the endodontic instrument in the heated environment.

In one embodiment, the placing step further includes placing the endodontic instrument in a heated gaseous environment having a gas temperature of from about 490° C. to about 510° C. wherein the gaseous environment preferably is ambient air. The method further may include a step of electropolishing the endodontic instrument prior to placing the instrument in the heated environment. In a preferred embodiment, the placing step further includes a step selected from the group consisting of heat treating the endodontic instrument for at least 120 minutes if the endodontic instrument has a core diameter ranging from about $1.9 \times 10^{-2}$ mm to about $3.1 \times 10^{-2}$ mm; heat treating the endodontic instrument for from at least 120 minutes to about 240 minutes if the endodontic instrument has a core diameter ranging from about $3.1 \times 10^{-2}$ mm to about $4.8 \times 10^{-2}$ mm; or heat treating the endodontic instrument for from at least 240 minutes to about 300 minutes if the endodontic instrument has a core diameter greater than about $4.8 \times 10^{-2}$ mm. In all of the embodiments, the instrument, after being exposed to the heated environment, is preferably allowed to cool using natural heat transfer mechanisms in ambient air.

In another aspect, embodiments of the disclosure provide an endodontic instrument with modified memory characteristics, the endodontic instrument made by the various method embodiments described above and including, for example, a method including the steps of placing an endodontic instrument in a heated environment having a temperature of from about 450° C. to about 550° C. for from about 90 to about 300 minutes, wherein the endodontic instrument is made from at least about 50% by mass of a superelastic alloy. In one embodiment, the step of placing the endodontic instrument in a heated environment further comprises placing the endodontic instrument in the heated environment for from about 180 minutes to about 300 minutes.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

FIG. 22 shows comparative angular deflection measurements including those involving nickel titanium instruments with no prior heat treatment or electropolishing step ("NT"), heat treated instruments with no prior electropolishing step ("NT+HT"), heat treated instruments that had undergone a prior electropolishing step ("NT+HT+EP"), and electropolished instruments with no prior heat treatment step (NT+EP), and the respective average values of these categories shown by the large dashed rectangular bars around each respective group of smaller bars;

FIG. 23A shows comparative cyclical fatigue measurements including the combined measurements of heat treated NiTi instruments with no prior electropolishing step ("HT") and electropolished instruments with no prior heat treatment step ("EP"), the sum of which are designated as "HT & EP (separate instruments; combined data)"; versus heat treated instruments that also underwent a prior electropolishing step, such instruments designated as "EP+HT (same instrument)"; the respective average values of these categories shown by the large dashed rectangular bars around each respective group of smaller bars;

FIG. 23B shows comparative torque measurements including the combined measurements of heat treated NiTi instruments with no prior electropolishing step ("HT") and electropolished instruments with no prior heat treatment step ("EP"), the sum of which are designated as "HT & EP (separate instruments; combined data)"; versus heat treated instruments that also underwent a prior electropolishing step, such instruments designated as "EP+HT (same instrument)"; the respective average values of these categories shown by the large dashed rectangular bars around each respective group of smaller bars

DETAILED DESCRIPTION

Various terms used herein are intended to have particular meanings Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

mN·m: the unit symbol for milli-Newton·meter.
m: the length unit symbol for meter.
mm: the length unit symbol for millimeter.

Working Portion:

That part of an endodontic instrument which includes surface features for removing material from a root canal including, but not limited to, surface features for scraping, shaving, cutting, penetrating, excavating, and/or removing material from canal wall surfaces in an effort to shape and/or enlarge a root canal.

Figure 1A:
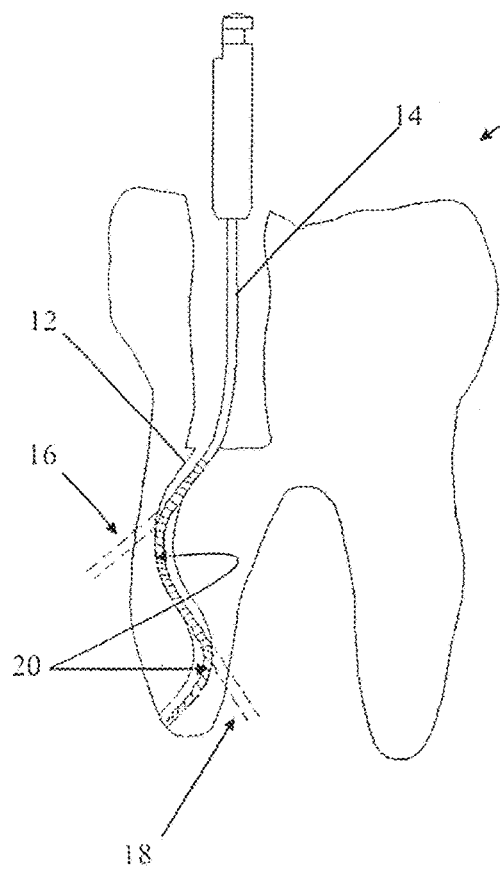
FIG. 1A shows a further somewhat schematic representation of a tooth root canal being operated on using a dental instrument.
Figure 1B:
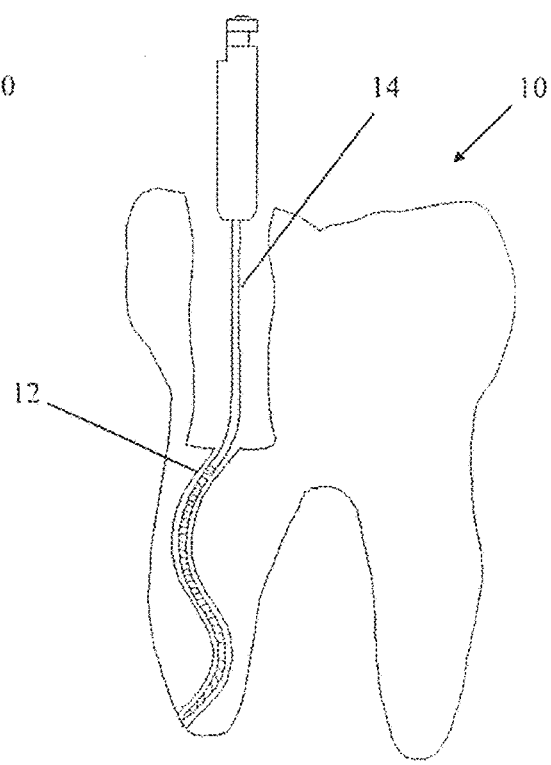
FIG. 1B shows a somewhat schematic representation of a tooth being operated on using a dental instrument.

FIGS. 1A and 1B show somewhat schematic representations of a tooth 10 including a natural root canal 12 in which an endodontic instrument 14 is being used to extirpate the natural root canal 12. When devices such as the endodontic instrument 14 shown in FIG. 1A are made from nickel-titanium (or "NiTi" or "Nitinol"), such devices tend to have improved flexibility properties relative to similar devices made of stainless steel. This property of NiTi and other similar alloys is sometimes referred to in part as superelasticity or psuedoelasticity and is often lauded as a unique and beneficial characteristic of endodontic files made from NiTi.

As FIG. 1A shows, however, when NiTi endodontic devices such as tapered files are used to navigate, for example, the natural root canal 12 of the tooth 10, the tendency of the device 14 to veer to a path contrary to the natural root canal 12 shape is a continuous concern for a dental practitioner—particularly when the instrument is used along a natural root canal with excessive curvature. A first deviation path 16 and a second deviation path 18 are shown in FIG. 1A to illustrate the manner in which an instrument made of NiTi tends to create disproportionate lateral forces along an inner surface 20 of the natural root canal 12 at certain locations. If this tendency is not carefully monitored by a dental practitioner, such instrument could easily (and often does) deviate from the natural root canal 12, boring an artificial structure which has the potential to compromise an entire tooth structure.

In an attempt to address the drawbacks associated with NiTi dental instruments as used in endodontic procedures discussed above, the inventor has performed a number of experiments in an effort to increase the beneficial flexibility properties of NiTi which, in turn, decreases the lateral forces exerted by a NiTi dental instrument on the inner surface of a tooth root canal. The inventor has surprisingly found a method for treating machined NiTi instruments that increases the flexibility of such instruments.

In a first study, the Applicant performed twenty five tests using ADA guidelines (discussed infra) on five groups of endodontic files for properties including torque and angular deflection to see if various heat treatment methods had any effect on the relative performance of the files. Trends of interest became apparent based on the visual "signature" of each set of data sets. Table 1 below indicates relationships between each group of tests with various parameters.

TABLE 1

| | Ave. Torque (mN · m) | Ave. Angular Deflection (Revolutions) |
| --- | --- | --- |
| Control Group | about 2 | 1.61 |
| Experimental Group 1 | less than 2 | 2.89 |
| Experimental Group 2 | unstable data | 3.32 |
| Experimental Group 3 | unstable data | 3.69 |
| Experimental Group 4 | about 2 | 4.05 |

Figure 2:
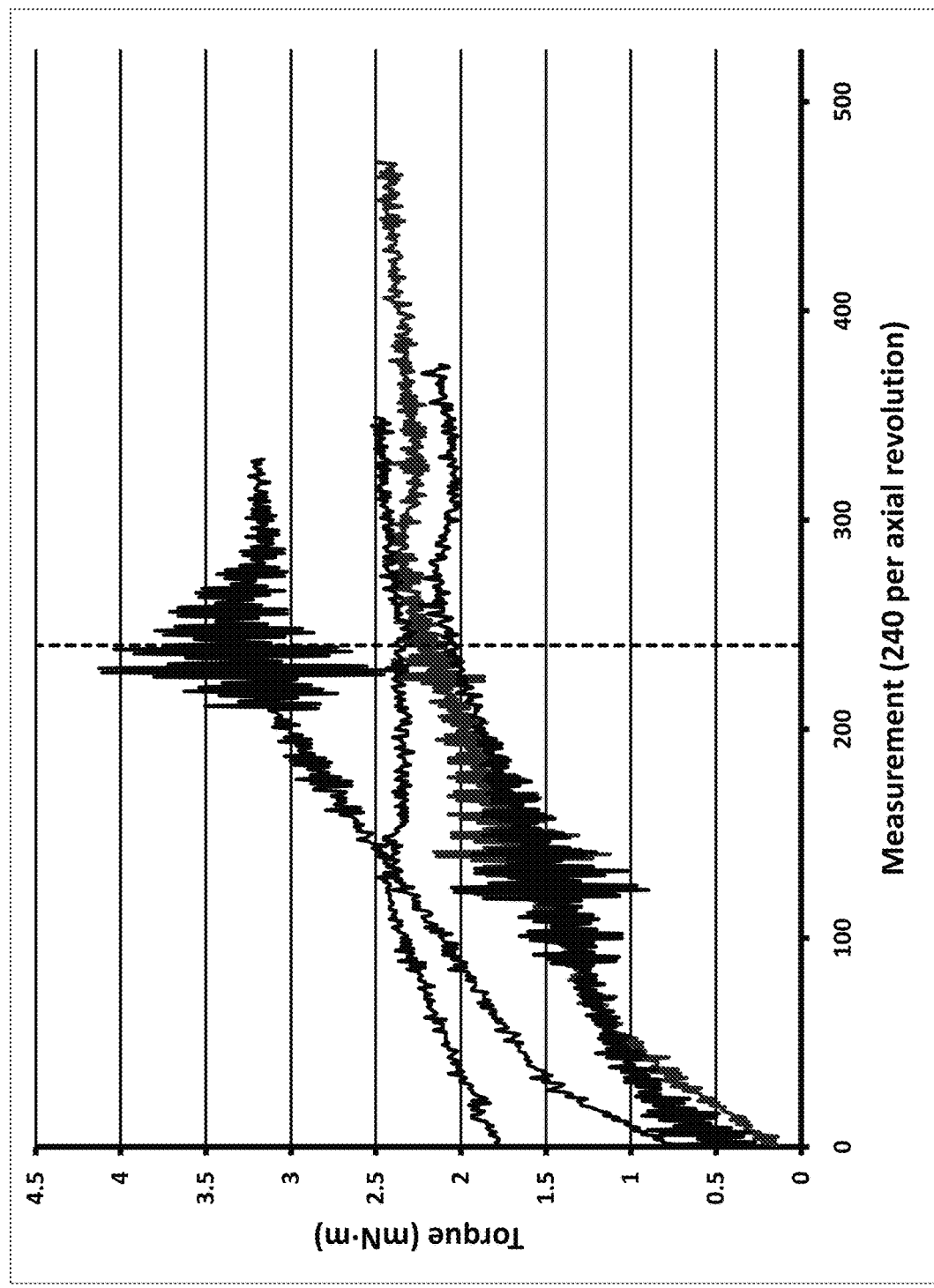
FIG. 2 shows a two-dimensional plot of torque data (vertical axis) versus angular deflection data (horizontal axis) for untreated ("control") NiTi instruments.
Figure 3:
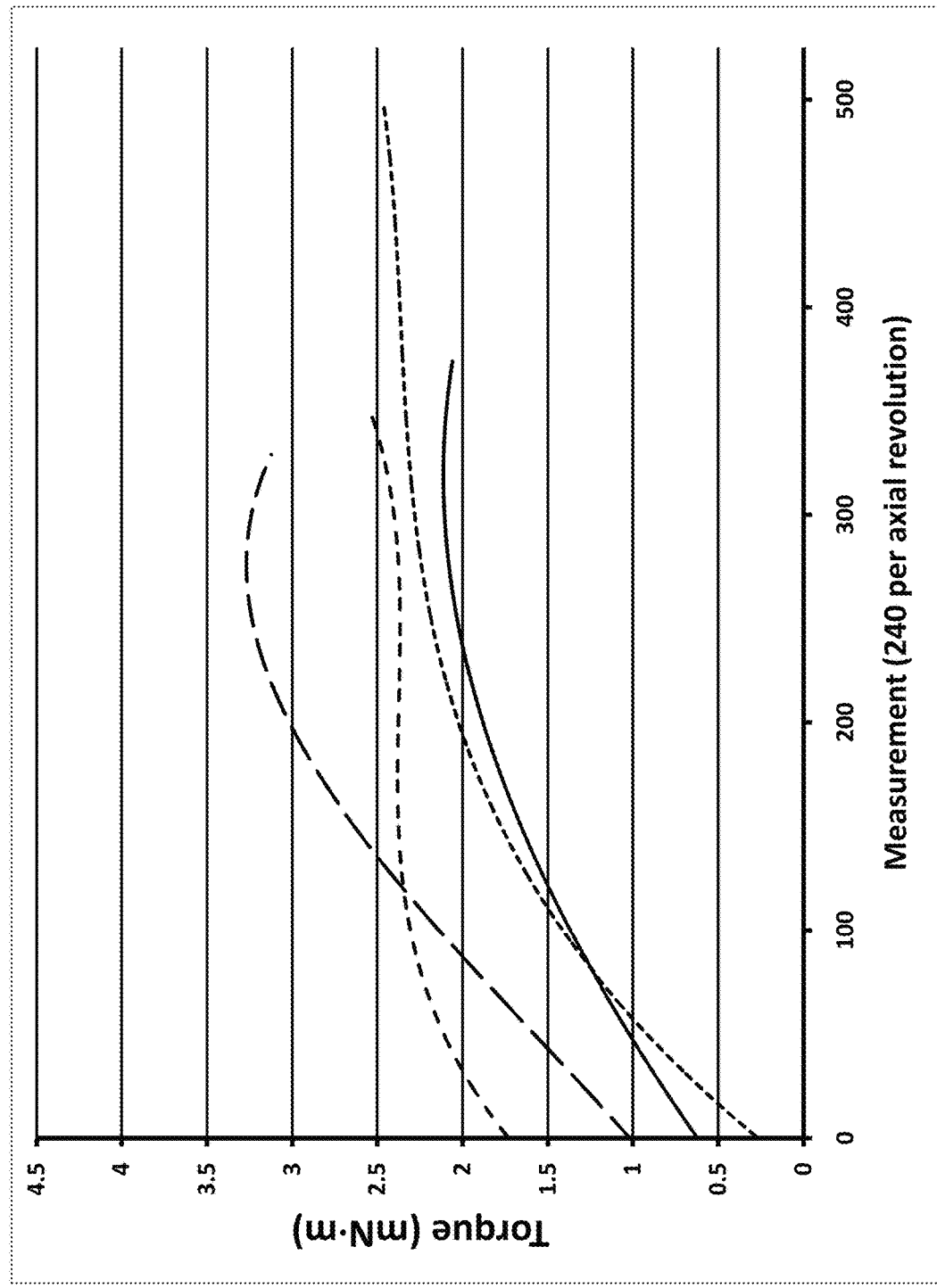
FIG. 3 shows a two-dimensional plot of the data in FIG. 2 wherein the data sets have been fitted to conform to third degree polynomial equation curves.

Graphs shown in FIGS. 2-8 plot torque (vertical axis) versus angular deflection (horizontal axis). In each of the graphs shown in FIGS. 2-8, 240 measurement samples for torque versus angular deflection were taken per one full axial (twisting) revolution of the instrument. FIG. 2 shows a graph of four data sets representing four separate test samples included in the control group which included only NiTi instruments that had not been heat treated according to Applicant's treatment method. A fifth data set in the control group was discarded because of a testing fault with the sample. As can be seen in FIG. 2, all of the test runs of the control group displayed a similar graphical signature which is more easily seen in FIG. 3 wherein the data associated with each test sample was used to generate a second order polynomial trend line.

Figure 4:
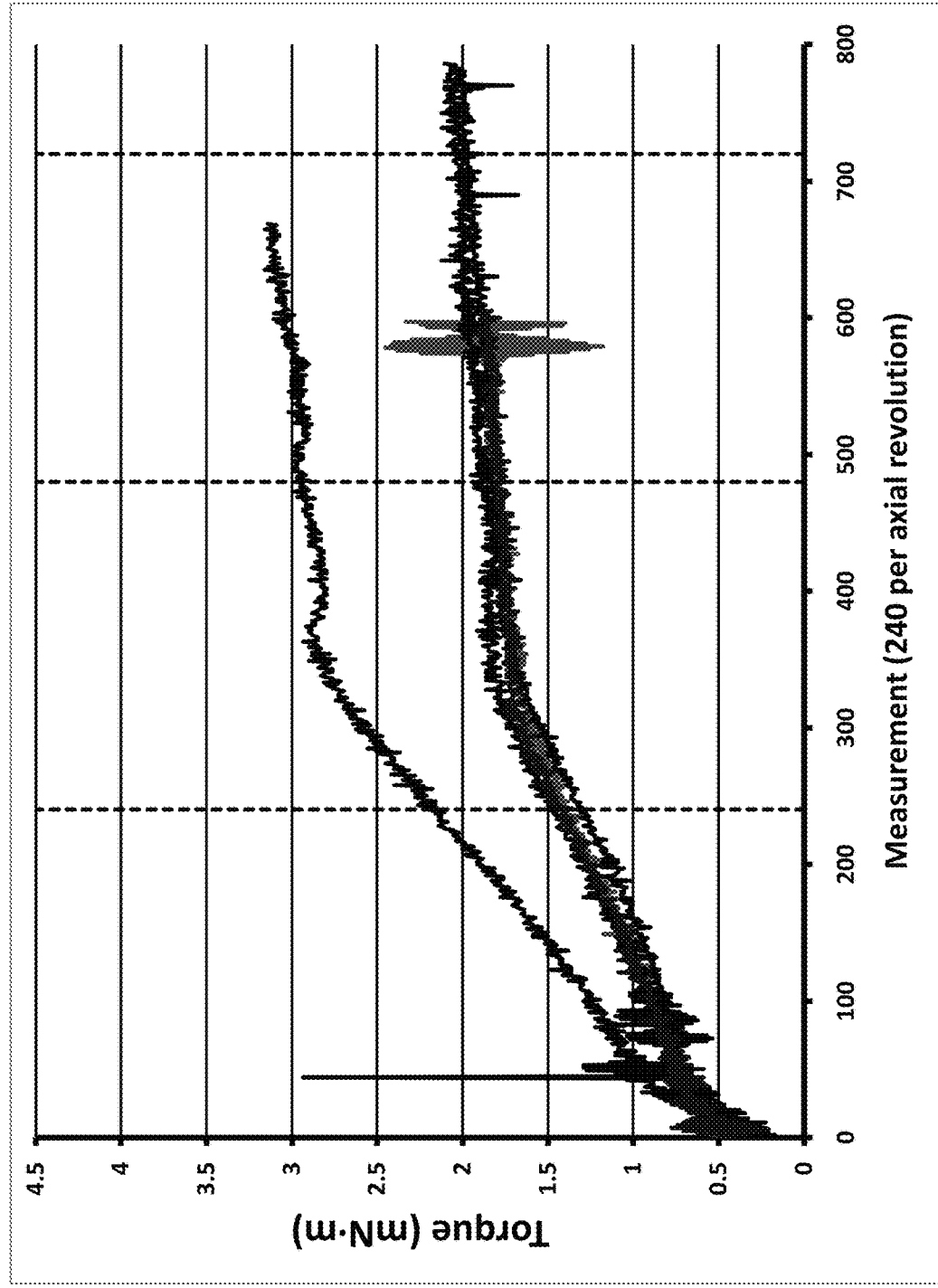
FIG. 4 shows a two-dimensional plot of torque data (vertical axis) versus angular deflection data (horizontal axis) for several NiTi instruments treated according to one embodiment of the invention.
Figure 5:
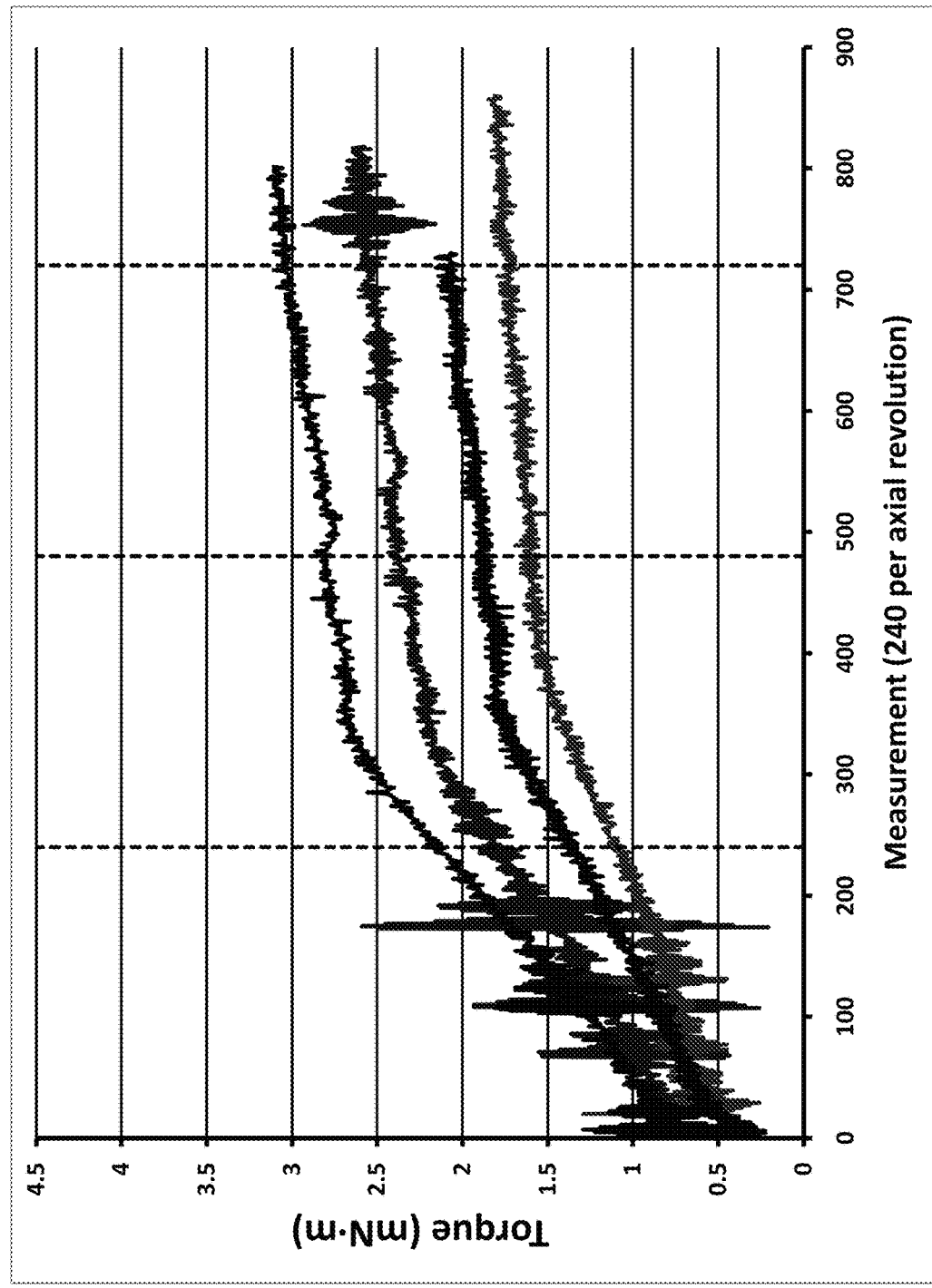
FIG. 5 shows a two-dimensional plot of torque data (vertical axis) versus angular deflection data (horizontal axis) for several NiTi instruments treated according to another embodiment of the invention.
Figure 6:
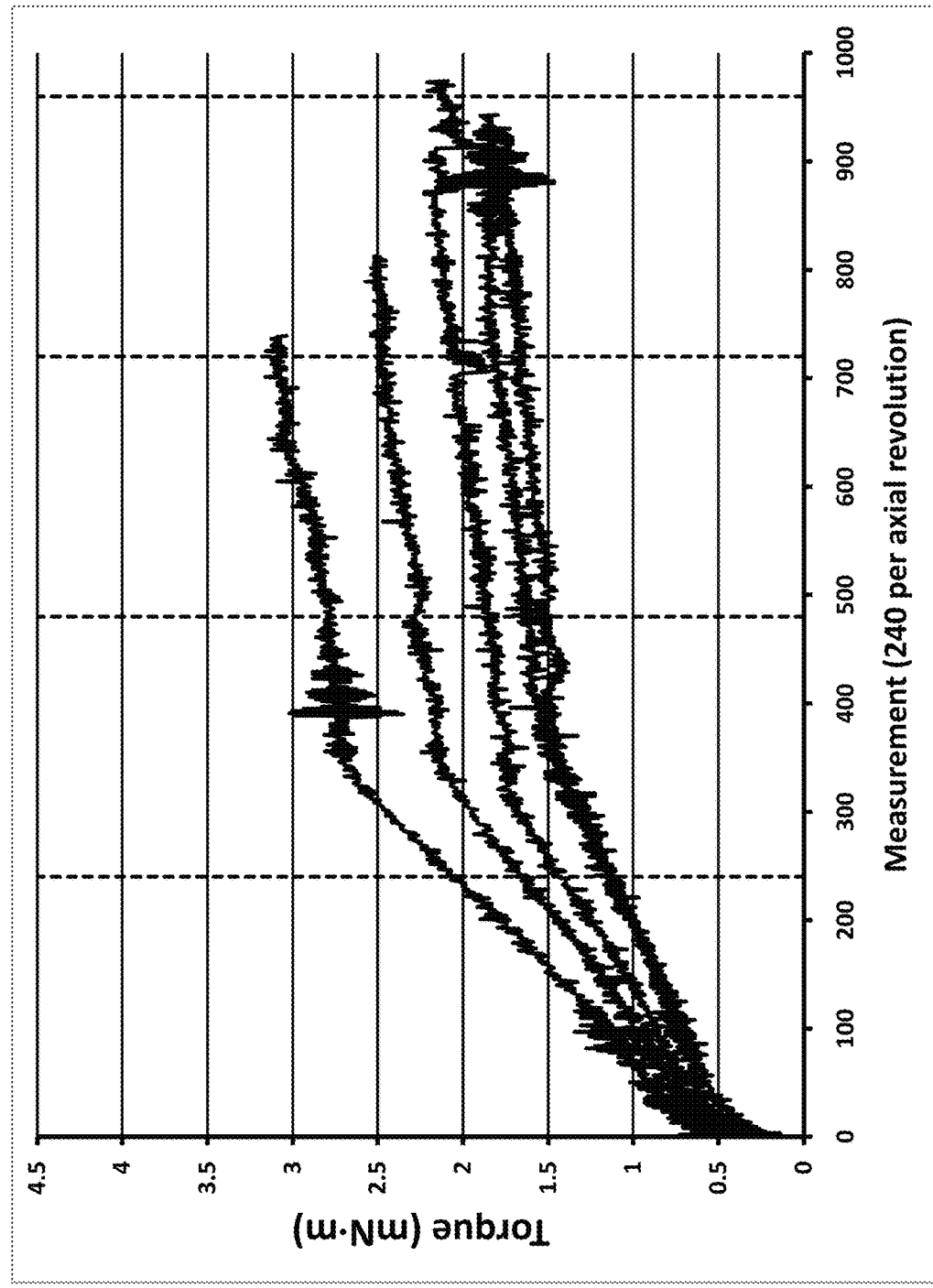
FIG. 6 shows a two-dimensional plot of torque data (vertical axis) versus angular deflection data (horizontal axis) for several NiTi instruments treated according to a further embodiment of the invention.
Figure 7:
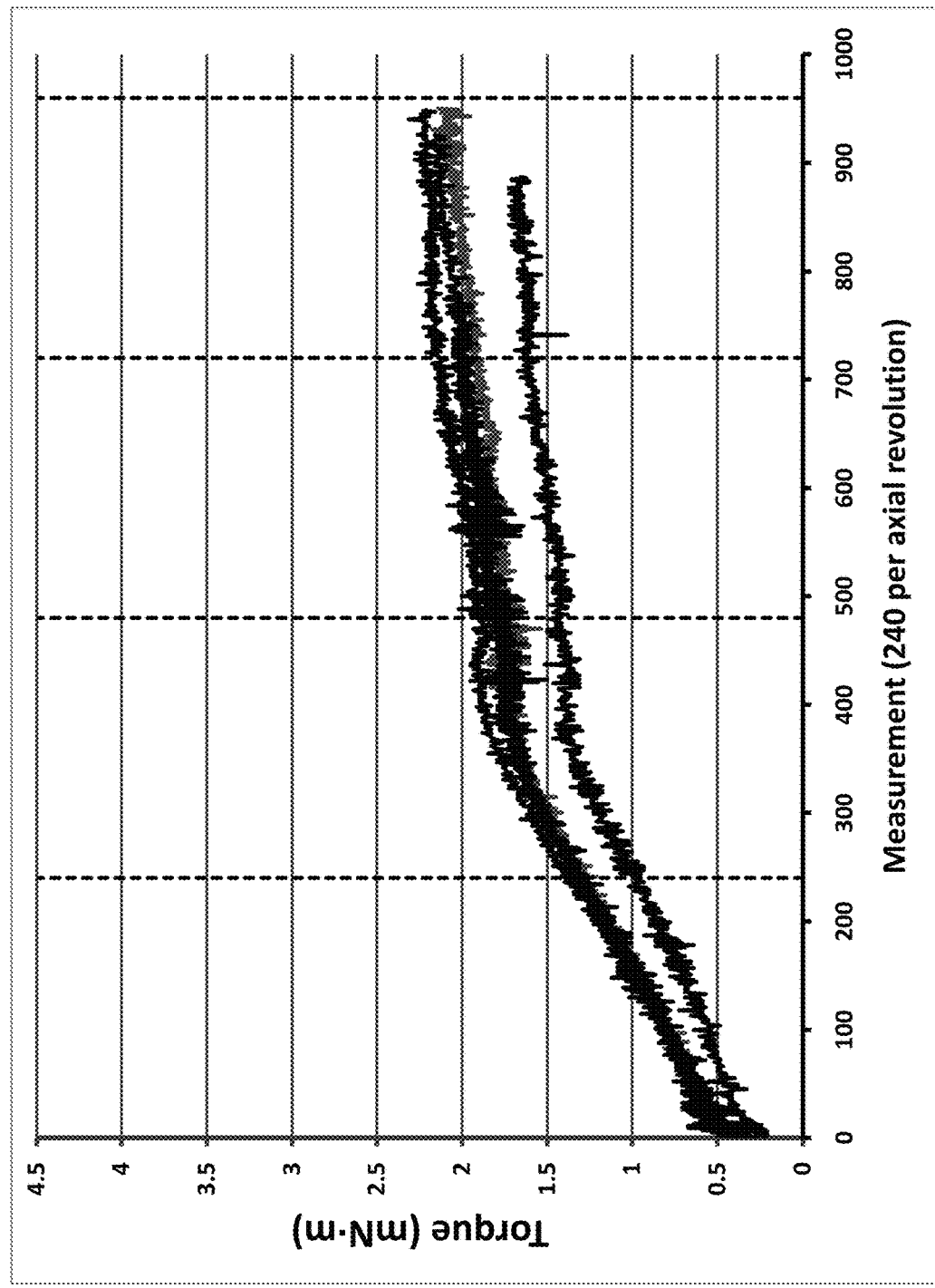
FIG. 7 shows a two-dimensional plot of torque data (vertical axis) versus angular deflection data (horizontal axis) for several NiTi instruments treated according to an additional embodiment of the invention.
Figure 8:
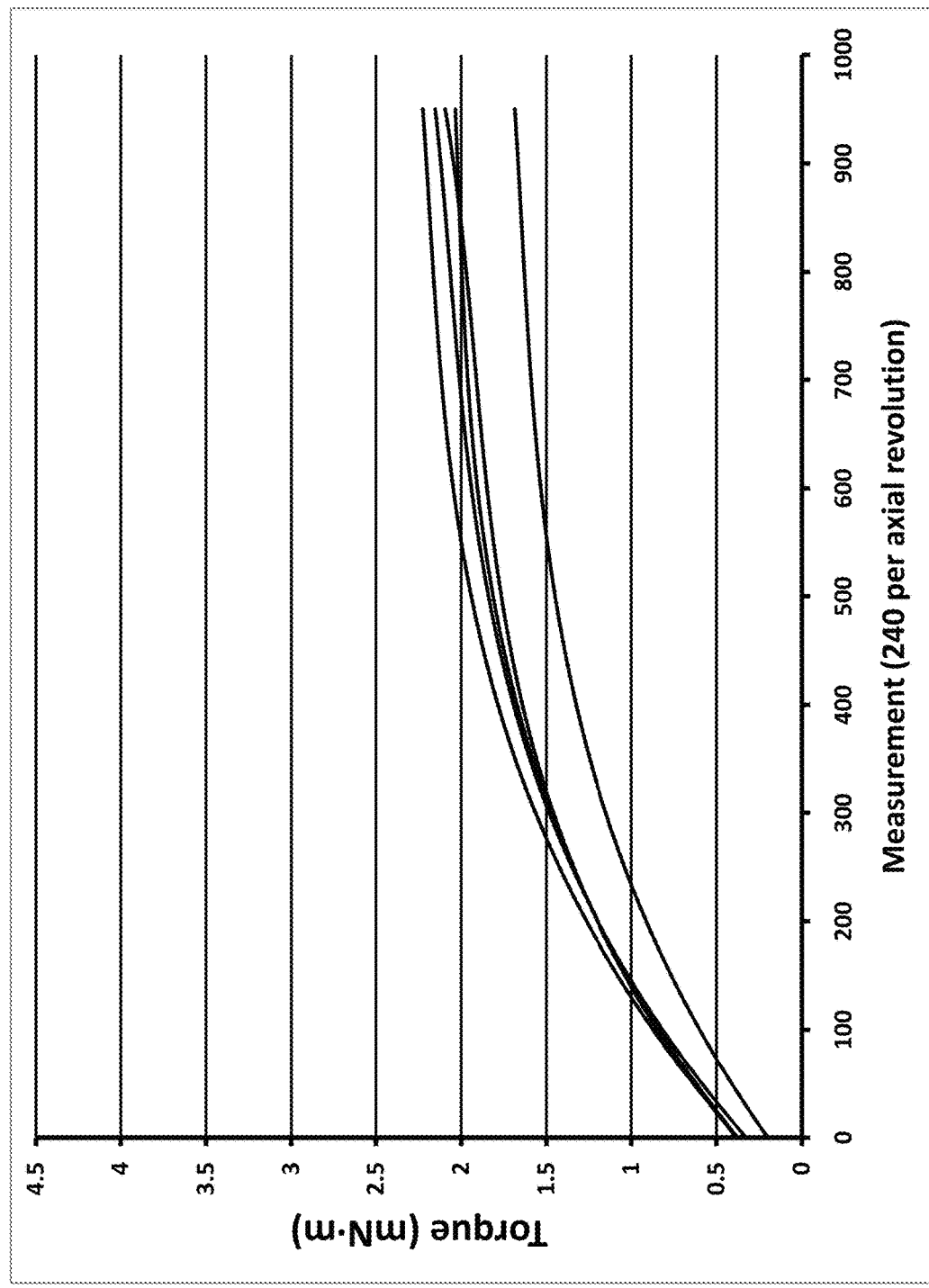
FIG. 8 shows a two-dimensional plot of the data in FIG. 7 wherein the data sets have been fitted to conform to third degree polynomial equation curves.

Each of FIGS. 4-8 show data sets of wire samples that have been heat treated by being placed in a stainless steel pan and inserted into an oven which was pre-heated to about 500° C. The difference between the experimental groups was the amount of time the test samples of a particular group were kept in the oven. FIG. 4, for example, shows a graph of five data sets representing five separate test samples included in the first experimental group which remained in the oven for 15 minutes. FIG. 5 shows a graph of five data sets representing five separate test samples included in the second experimental group which remained in the oven for 45 minutes. FIG. 6 shows a graph of five data sets representing five separate test samples included in the third experimental group which remained in the oven for 90 minutes. FIG. 7 shows a graph of five data sets representing five separate test samples included in the fourth experimental group which remained in the oven for 120 minutes. FIG. 8 shows second order polynomial trend lines based on the data sets of the fourth experimental group so that the respective "signatures" of these data sets can be more clearly seen relative to one another.

Although the average torque value of the fourth experimental group was very similar to the average torque value of the control group, it was surprisingly discovered that the average angular deflection of the fourth experimental group demonstrated an increase of almost 250% relative to the average angular deflection of the control group. Additionally, the samples tested in the fourth experimental group demonstrated a cyclical fatigue of about 120 seconds as compared to about 30 seconds as demonstrated with respect to the samples tested in the control group. Also, the visual signatures of the individual data sets in FIG. 7 and FIG. 8 were more precisely aligned as best shown in FIG. 8. As a follow-up to the test results given above, more testing was performed with a focus on heating machined endodontic NiTi instruments as described above for about 120 minutes and gathering additional data.

The purpose of the additional analysis was to build upon the experimentation discussed above in which the inventor was able to modify certain physical properties of Nickel-Titanium through a specific heating process. Some goals for the additional tests are shown below in Table 2.

TABLE 2

| TEST ITEM | NAME | CRITERIA | ACCEPTANCE |
| --- | --- | --- | --- |
| 1 | Torque | 1.77 Minimum | Must pass Minimum Criteria per ADA 101 |
| 2 | Angular Deflection | 360° Minimum | Must pass Minimum Criteria per ADA 101 |
| 3 | Cyclical Fatigue | 10-Series Equivalent | Must be greater than Industry equivalence |
| 4 | Flexibility | 10-Series Equivalent | Must be less than Industry equivalence |
| 5 | Clinician Feedback | Inquiry | Positive Feedback |

Figure 9:
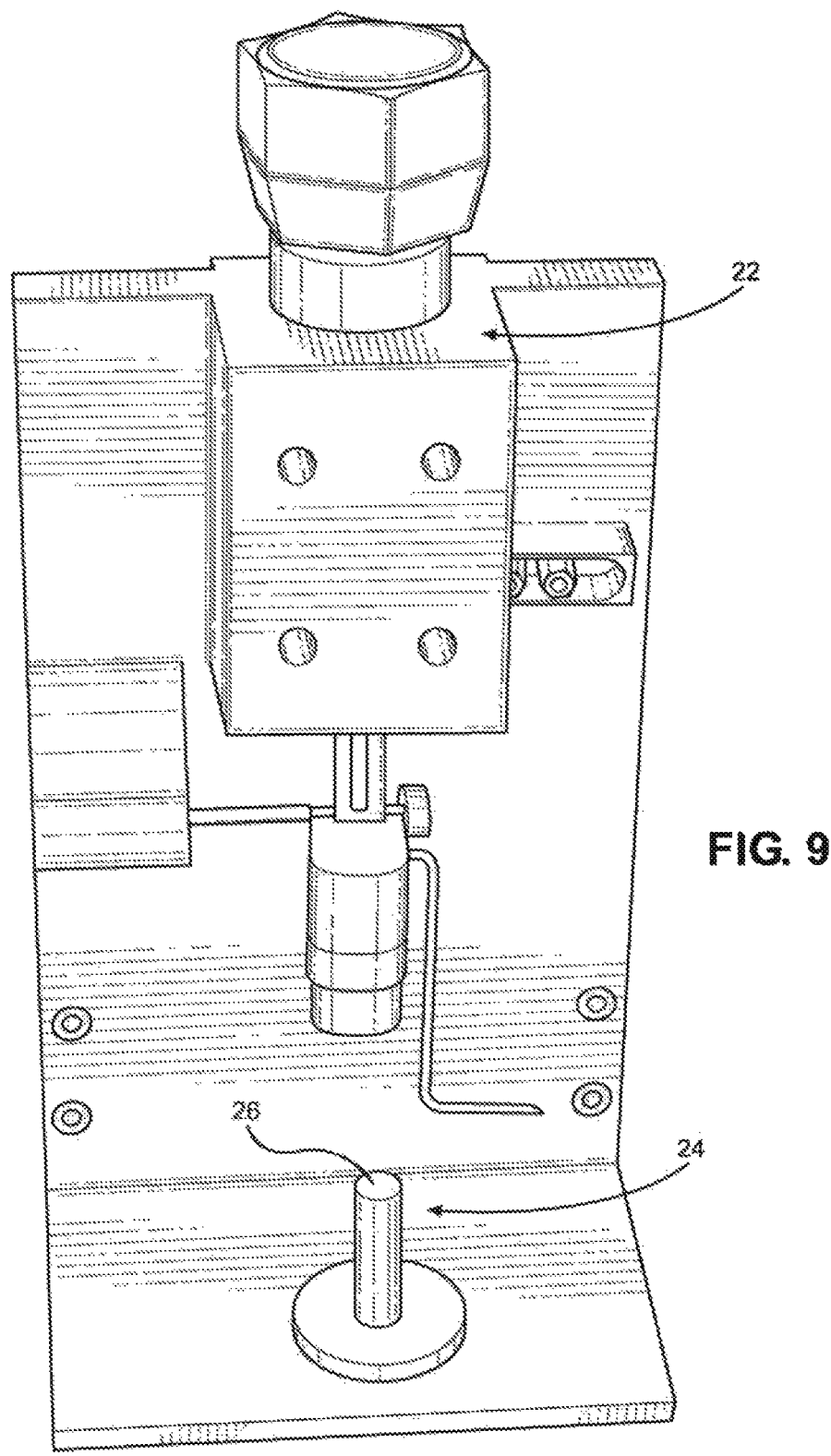
FIG. 9 shows an apparatus used to test cyclical fatigue of a dental instrument.

The additional testing followed the guidelines found in ADA no. 28 (sections 6.4 and 6.5), ADA no. 101, and ISO 3630-1 (sections 7.4 and 7.5), the contents of which are incorporated herein by reference in their entireties. Cyclical fatigue testing is not an ISO standard test, but it has been utilized in the testing of rotary Nickel-Titanium instruments over the past few years. Such cyclical fatigue testing includes a motor unit 22 as shown in FIG. 9 set at, for example, about 300 rpm to simulate the speed of an instrument as used during, for example, a root canal procedure. A Ni—Ti test instrument is lowered into a simulated canal structure 24 which may be set at about 90° relative to the plane of rotation of the test instrument, until the depth of a calibration line along the test instrument is reached at, for example, about 19 millimeters in reference to a first end 26 of the simulated canal structure 24. The amount of time the test instrument is rotated prior to breaking or otherwise failing is recorded so as to determine how long it took, under controlled conditions, for the test instrument to break.

No less than twenty machined endodontic NiTi instruments which had been heat treated in a 500° C. oven for about 120 minutes were tested according to the criteria set forth above in Table 2. More specifically, the tested instruments were 10 Series™ endodontic files offered by D&S Dental, LLC of Johnson City, Tenn., the files having a total length of about 25 mm, a working length of about 10 mm, and a taper rate of 0.04 mm/mm. An important aspect of the method described herein is heat treating after machining of a NiTi dental instrument has a profound effect on the physical properties of the machined instrument. Table 3A below summarizes the test results.

TABLE 3A

| ITEM | NAME | CRITERIA | RESULTS | COMMENTS |
| --- | --- | --- | --- | --- |
| 1 | Torque | 1.77 mN · m Minimum | Worst Case 4 mN · m. | Passed |
| 2 | Angular Deflection | 360° Minimum | Worst Case 510° | Passed |
| 3 | Cyclical Fatigue | 10-Series 25 seconds @ 90° | Mean of 160.79 seconds with a Standard Deviation of 38 seconds | Passed |
| 4 | Flexibility | 10-Series 50 mN · m @ 45° | Mean of 18 mN · m @ 45° | 5 pieces were tested for amount of torque needed to reach 45°. Passed |
| 5 | Clinician Feedback | Inquiry | Pros: Good Cutting ability, No breakage Cons: Too flexible, loss of tactile feel | Marginal |

The test results overall showed notable improvement in all categories listed in Table 3A. Table 3B shows specific product comparisons between different brands of endodontic instruments. The torque measurements for instruments treated using the method described above were all still well above the minimum standards set forth in ADA no. 28 (sections 6.4 and 6.5), ADA no. 101, and ISO 3630-1 (sections 7.4 and 7.5).

TABLE 3B

| With CM ™ Process | Torque (mN · m) | Without CM ™ Process | Torque (mN · m) |
| --- | --- | --- | --- |
| 10-Series 25_04 | 4.4995 | 10-Series 25_04 | 7.0307 |
| 10-Series 40_04 | 13.3086 | 10-Series 40_04 | 21.9641 |
| Typhoon 25_04 | 1.6006 | Typhoon 25_04 | 3.1405 |
| Typhoon 40_04 | 5.2195 | Typhoon 40_04 | 9.4911 |
| (no data) | (no data) | Twisted 25_04 | 1.4918 |
| (no data) | (no data) | Twisted 40_04 | 3.4895 |
| (no data) | (no data) | Vortex 25_04 | 3.3289 |
| (no data) | (no data) | Vortex 40_04 | 9.7674 |

Figure 10:
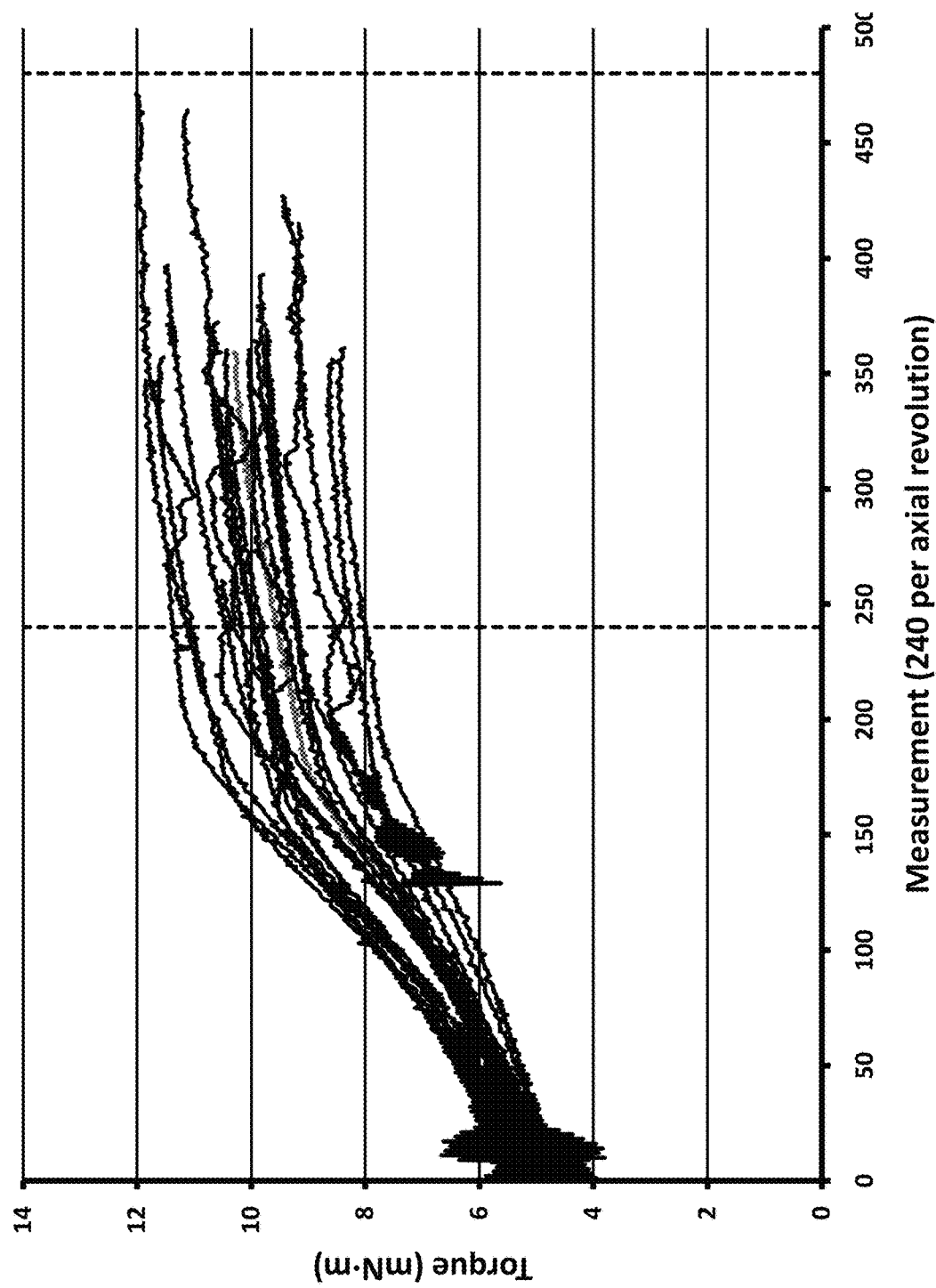
FIG. 10 shows a two-dimensional plot of torque data (vertical axis) versus angular deflection data (horizontal axis) for twenty NiTi instruments treated according to an embodiment of the invention.
Figure 11:
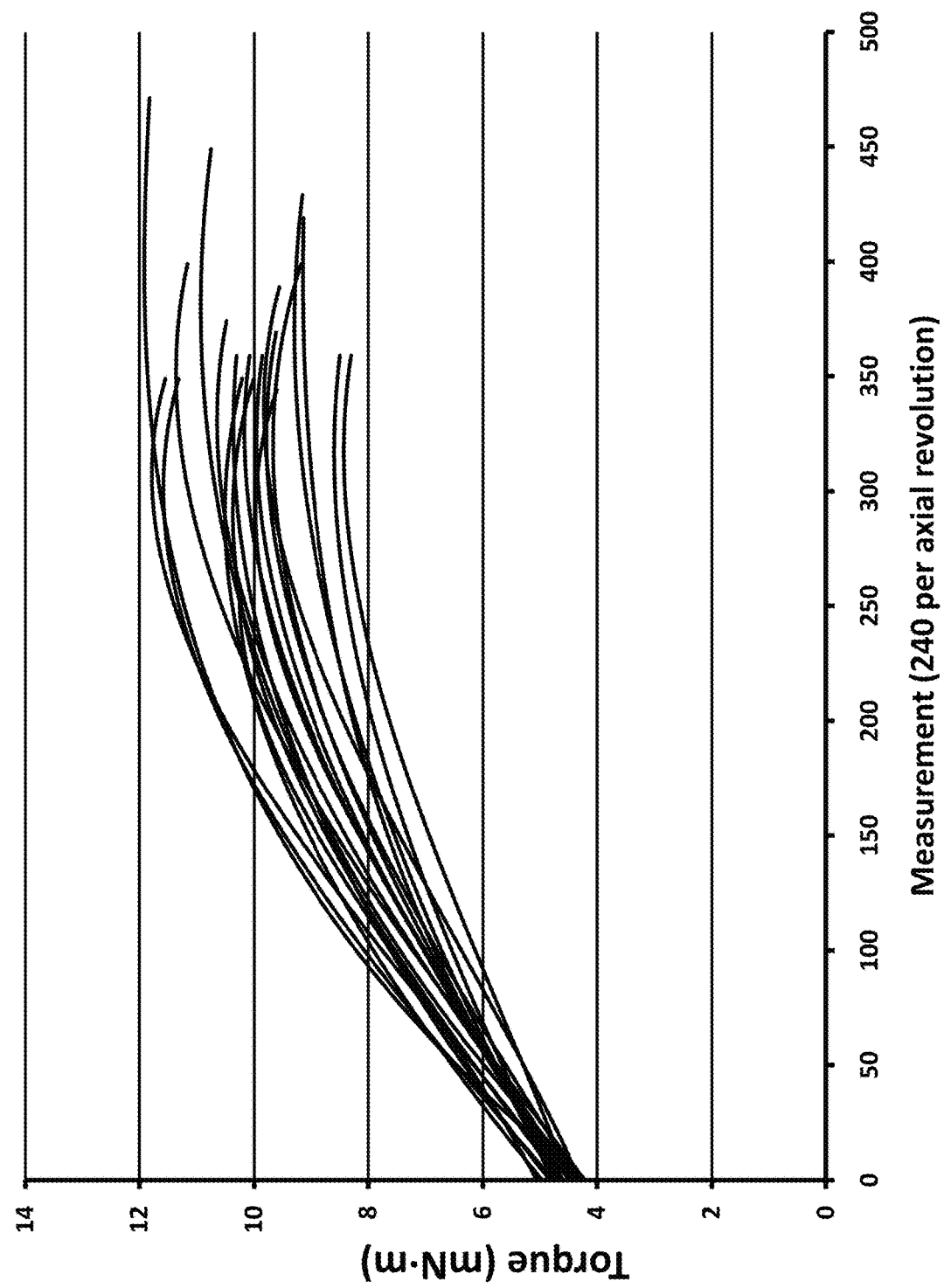
FIG. 11 shows a two-dimensional plot of the data in FIG. 10 wherein the data sets have been fitted to conform to third degree polynomial equation curves.
Figure 12:
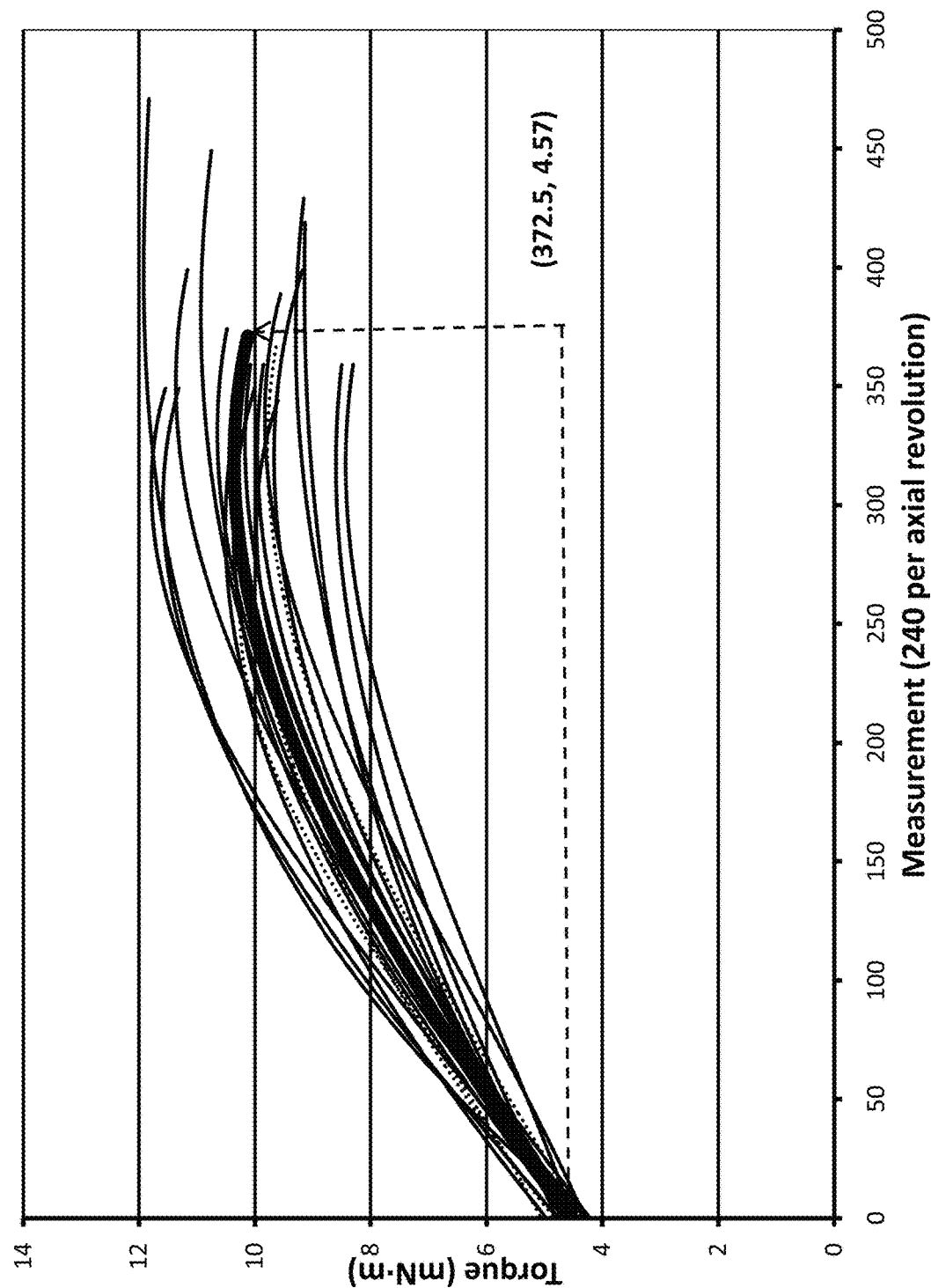
FIG. 12 shows the two-dimensional plot of torque data (vertical axis) versus angular deflection data (horizontal axis) shown in FIG. 11 further including a superimposed curve generated from the average values of the coefficients for the third degree polynomial equations used to fit the data from FIG. 10 in the curves shown in FIG. 11.

The graph shown in FIG. 10 shows the twenty samples as plotted with respect to torque (vertical axis) versus angular deflection wherein 240 data measurements were taken per one 360° (axial) revolution of a tested sample. FIG. 11 shows trendlines plotted based on third order polynomial equations to best model the data results for each test sample. FIG. 12 shows the trendlines from FIG. 11 along with a bold trendline generated and plotted based on the average values of the twenty trend lines representing each test sample. Table 4 shows the model equations used to generate each trendline in FIG. 11 as well as the equation used to generate and plot the bold trendline in FIG. 12.

TABLE 4

Coefficients as used in a third order polynomial equation $f(x) = Ax^3 + Bx^2 + Cx + D$.

| Test Sample | Coefficients | | | |
| --- | --- | --- | --- | --- |
| | A | B | C | D |
| 1 | −0.00000008 | −0.000004 | 0.0271 | 4.4365 |
| 2 | −0.00000008 | −0.000005 | 0.0291 | 4.4036 |
| 3 | −0.0000001 | 0.00002 | 0.0152 | 4.4996 |
| 4 | −0.0000001 | −0.000004 | 0.0346 | 4.7673 |
| 5 | −0.00000002 | −0.00004 | 0.0321 | 4.8333 |
| 6 | −0.00000005 | −0.000007 | 0.0195 | 4.7131 |

TABLE 4-continued

Coefficients as used in a third order polynomial equation $f(x) = Ax^3 + Bx^2 + Cx + D$.

| Test Sample | A | B | C | D |
|---|---|---|---|---|
| 7 | −0.00000008 | −0.0000006 | 0.0253 | 4.3494 |
| 8 | 0.00000007 | −0.0001 | 0.0491 | 4.2493 |
| 9 | −0.00000008 | −0.000005 | 0.0314 | 4.2093 |
| 10 | −0.0000001 | 0.00004 | 0.0182 | 4.3039 |
| 11 | −0.0000001 | −0.000007 | 0.0305 | 4.6517 |
| 12 | −0.00000008 | −0.0000002 | 0.0252 | 4.6123 |
| 13 | −0.0000002 | 0.00003 | 0.03 | 4.6047 |
| 14 | −0.00000002 | −0.00002 | 0.0224 | 4.7004 |
| 15 | 0.00000003 | −0.00006 | 0.0287 | 4.5002 |
| 16 | −0.00000007 | −0.000003 | 0.0243 | 4.5967 |
| 17 | −0.0000003 | 0.00008 | 0.0209 | 5.063 |
| 18 | 0.00000002 | −0.00006 | 0.038 | 4.2322 |
| 19 | −0.0000002 | 0.00006 | 0.0285 | 4.7873 |
| 20 | −0.00000006 | −0.00003 | 0.033 | 4.9694 |

Based on the results of the follow-up tests, the average torque value for the samples tested was about 4.57 mN·m. The average number of measurements taken prior to instrument failure was 372.5 which corresponds to about 1.5 full axial revolutions (i.e., 372.5 measurements÷240 measurements per axial revolutions). The values are shown in FIG. 12.

The results of the tests carried out above are promising because they demonstrate that heat treating an endodontic instrument to about 500° C. for about two hours or more after machining has taken place results in improved instrument flexibility. Such increased flexibility leads to an instrument such as the treated instrument 14' shown in FIG. 1B to more closely follow the natural root canal 12 of the tooth 10 and exhibit less lateral forces along the inner surface of such root canal 12.

Figure 19:
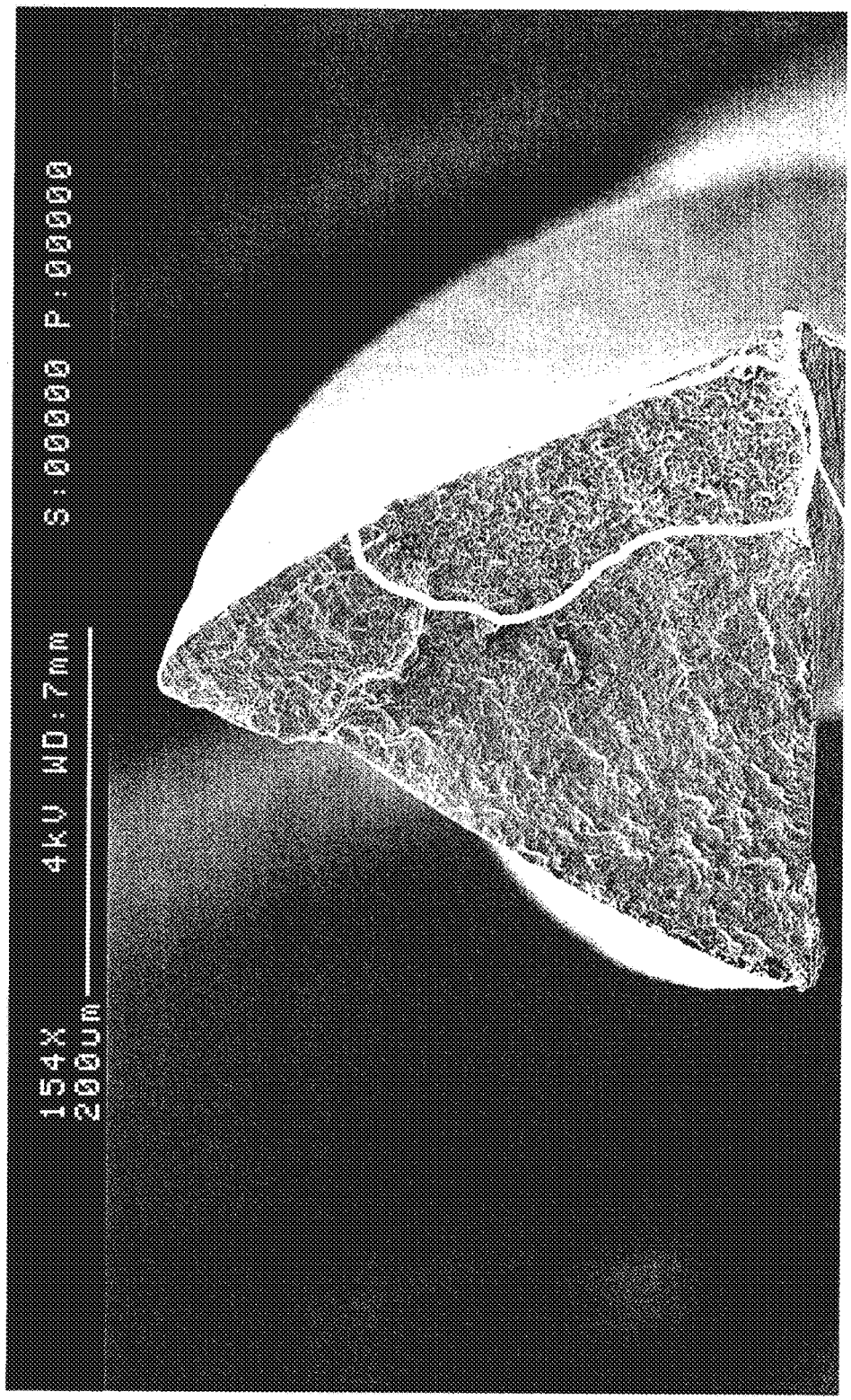
FIG. 19 shows the torn cross section of a heat treated endodontic instrument after testing wherein the instrument had been heat treated according to an embodiment of the invention prior to such testing.

One specific example of improved cyclical fatigue is shown in FIG. 19 showing the torn cross section of a heat treated endodontic instrument tested at a speed 300 rpm, and dry (i.e., no irrigation solution). This testing was conducted for Applicants by the Department of Oral Biological & Medical Sciences at the University of British Colombia in Vancouver, British Colombia. The micrographs show that the instrument fractured, but a small portion 28 of the instrument held together and maintained the integrity of the instrument for an extended period of time such that the test lasted for over 3000 cycles. Typical NiTi instruments usually completely separate upon a relatively small fracture occurs, but the heat treated instrument shown in FIG. 19 behaved differently and maintained its integrity with a large and deep fracture for more than enough time for a user to have realized that the instrument was mechanically failing.

The improved cyclical fatigue measurements (as compared to untreated NiTi instruments) strongly suggests that endodontic instruments treated according to embodiments described herein will last longer and endure more stress prior to failing. This enhancement translates into less time spent extracting broken bits of instruments and more time accomplishing the goal of a particular endodontic procedure.

In one embodiment, a method is disclosed for treating medical instruments including placing a medical instrument into an environment held at least at about 450° C. to about 550° C., more preferably from about 475° C. to about 525° C., and most preferably from about 490° C. to about 510° C. for a period of from about 90 minutes to about 180 minutes and more preferably from about 120 minutes to about 150 minutes. The dental instrument is preferably an endodontic instrument made from at least about 50% of a superelastic alloy, and the instrument is preferably a file, reamer, or a broach. Alternatively, the dental instrument can also include a plugger or a spreader. As another alternative, the dental instrument can include an orthodontic tool, wire, and/or appliance. The superelastic alloy is preferably Nickel-Titanium. The heat treated medical instrument preferably is placed in a metal pan with freedom of movement during the heating step. In this and other related embodiments, no special treatment atmosphere is required and, in a preferred embodiment, simple air is used. Similarly, unlike other processes that require special quenching steps to obtain desired properties, Applicants' embodiments require no quenching steps. Heated instruments are preferably brought to ambient air temperature by natural conduction, convection, and radiation heat transfer.

Applicants have determined that the duration of heat treatment described herein is preferably a function of the core diameter of the instrument being treated. For example, instruments with core diameters ranging from about $1.9 \times 10^{-2}$ mm to about $3.1 \times 10^{-2}$ mm are preferably heat treated for at least 120 minutes; instruments with core diameters ranging from about $3.1 \times 10^{-2}$ mm to about $4.8 \times 10^{-2}$ mm are preferably heat treated for from at least 120 minutes to about 240 minutes; and instruments with core diameters greater than about $4.8 \times 10^{-2}$ mm are preferably heat treated for from at least 240 minutes to about 300 minutes. These ranges overlap somewhat because other factors also determine the effectiveness the heat treatment process including, for example, the particular helix angle(s) of an endodontic instrument.

In a related embodiment, flexibility of an elongate machined medical instrument is varied along its length axis by heat treating only one or more discrete portions of the medical instrument. In the following examples, it is to be assumed that the medical instrument is an endodontic instrument including a working portion approximately 10 mm in length, such 10 mm length including a distal end (tip) and a flute length end (rear), wherein the second end is adjacent a non-working portion of the endodontic instrument. The assumptions given herein are for illustrative purposes only and are not intended as a limitation on the technology as described herein.

In a first example, an endodontic instrument made from primarily a superelastic alloy such as NiTi may be selectively heat treated along about 2 mm adjacent the distal end (tip) of the instrument, resulting in an instrument with a tip having enhanced flexibility with the remainder of the instrument remaining relatively rigid.

In another example, an endodontic instrument made from primarily a superelastic alloy such as NiTi may be selectively heat treating a discrete cross section of an instrument having a length of about 1 mm to about 2 mm located about 5 mm from the tip of the instrument. This will result in a relatively rigid tip, flexible middle portion, and relatively rigid end portion of the working portion of the instrument.

In yet another example, an instrument is heat treated from the tip of the instrument to about 2 mm from the tip as well as heat treated from about 9 mm to about 10 mm from the tip of the instrument. This example would result in an instrument with relative flexibility near the tip, relative rigidity along a midsection of the working portion of the instrument (i.e., from about 3 mm from the tip to about 8 mm from the tip), and relative flexibility from about 9 mm to about 10 mm from the tip of the instrument.

Figure 20:
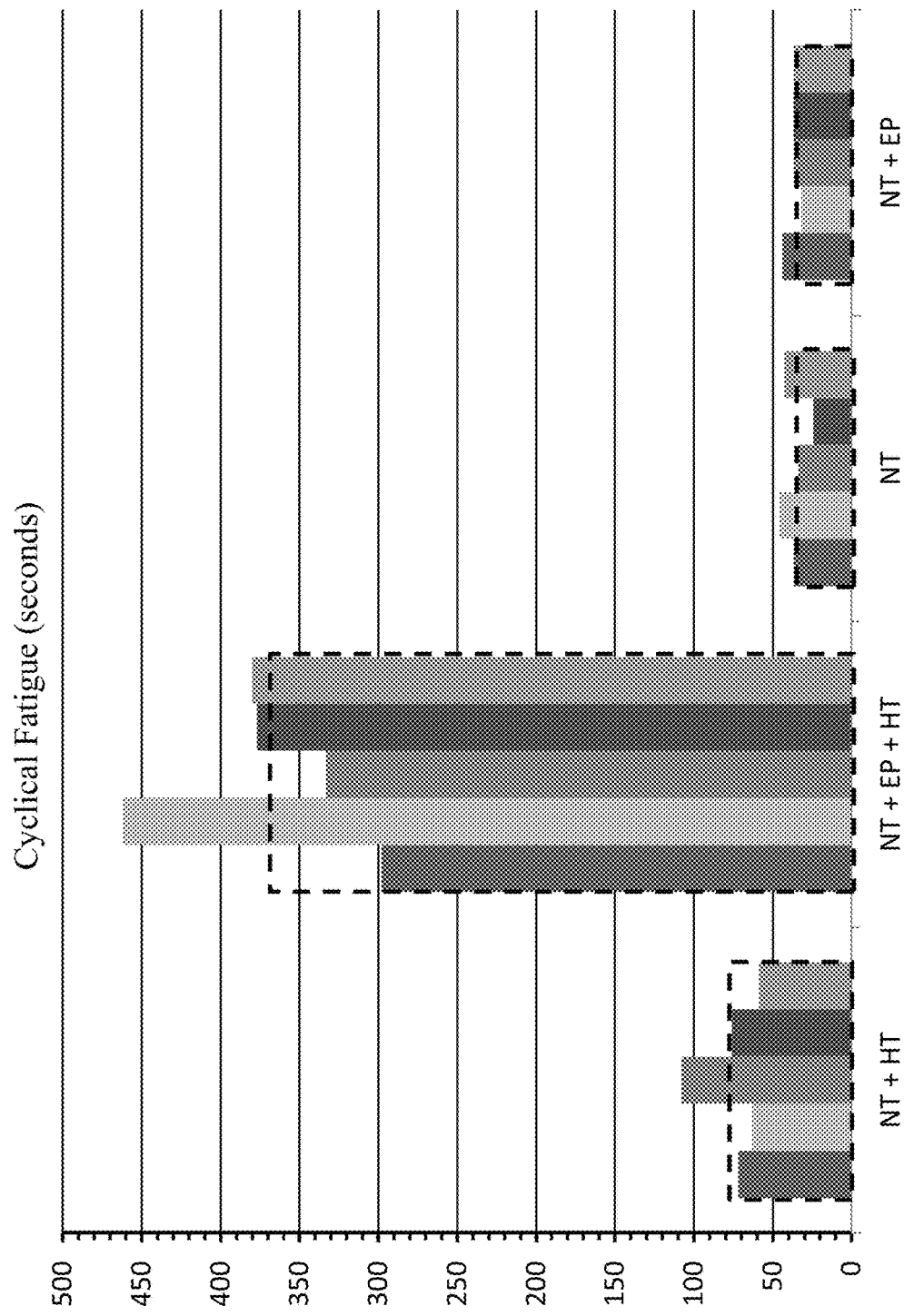
FIG. 20 shows comparative cyclical fatigue measurements including those involving nickel titanium instruments with no prior heat treatment or electropolishing step ("NT"), heat treated instruments with no prior electropolishing step ("NT+HT"), heat treated instruments that had undergone a prior electropolishing step ("NT+HT+EP"), and electropolished instruments with no prior heat treatment step (NT+EP), and the respective average values of these categories shown by the large dashed rectangular bars around each respective group of smaller bars.

In another example illustrated in FIG. 20, an instrument such as an apex locating apparatus is heat treated from the tip of the instrument to about 4 mm to about 5 mm from the tip. This example would result in an instrument with relative flexibility near the tip. In an apex locating apparatus, the relative flexibility of the tip allows the tip of the apparatus to more gingerly navigate the root canal of a tooth to locate the apical foramen of such tooth without puncturing through or beyond the canal itself.

FIG. 20 shows an example of a kit 40 of endodontic tools, the kit 40 in FIG. 20 including a plurality of endodontic tools 42 (42A-42D) having varying sizes and shapes for conforming to various root canal profiles. The plurality of endodontic tools 42 have controlled memory properties as a result of their NiTi composition and the manner in which the endodontic tools have been treated according to the treatment methods discussed above, along a memory section 44 of each endodontic tool. The memory section 44 preferably ranges from the tip of each tool to about 4 mm to about 10 mm from the tip of each tool. As illustrated in FIG. 20, a first endodontic tool 42A and a second endodontic tool 42B in the kit 40 have substantially constant diameters (shown as 46A and 46B). A third endodontic tool 42C and a fourth endodontic tool 42D have tapered diameters (shown as 46C and 46D). The tapered diameter 46C of the third endodontic tool 42C preferably ranges from about 0.005 mm/mm to about 0.015 mm/mm, and most preferably is about 0.01 mm/mm. The tapered diameter 46D of the fourth endodontic tool 42D preferably ranges from about 0.01 mm/mm to about 0.03 mm/mm, and most preferably is about 0.02 mm/mm. The endodontic tools 42 each preferably have a memory section 50 (50A-50D), the memory section preferably ranging in length from at least about 4 mm to about 12 mm from the tip of the endodontic tool. The endodontic tools 42 also preferably have a pointed tip section 52 (52A-52D) to enable each tool to reach the apical foramen of a tooth. The pointed tip section 52 preferably has an angle λ ranging from about 20° to about 40° and most preferably an angle of about 30°.

Other discrete treatment options are contemplated herein for treatment of specific axial cross-sections of an endodontic instrument to effect specific physical property alterations along the instrument's length as desired. The specific treatment may be accomplished using focused energy at certain points along an endodontic instrument and/or placing a resistance forming layer or layers on sections of an instrument that are not to be heat treated.

In addition to the treated endodontic instruments and related methods described above, a related embodiment includes a step of electropolishing an endodontic instrument prior to the various heat treatments described above. Electropolishing is a technique that has been used in the art for the purpose of removing surface flaws in endodontic instruments. However, Applicants have surprisingly found that electropolishing an endodontic instrument prior to heat treating the endodontic instrument as described above results in improved instrument characteristics.

Figure 13:
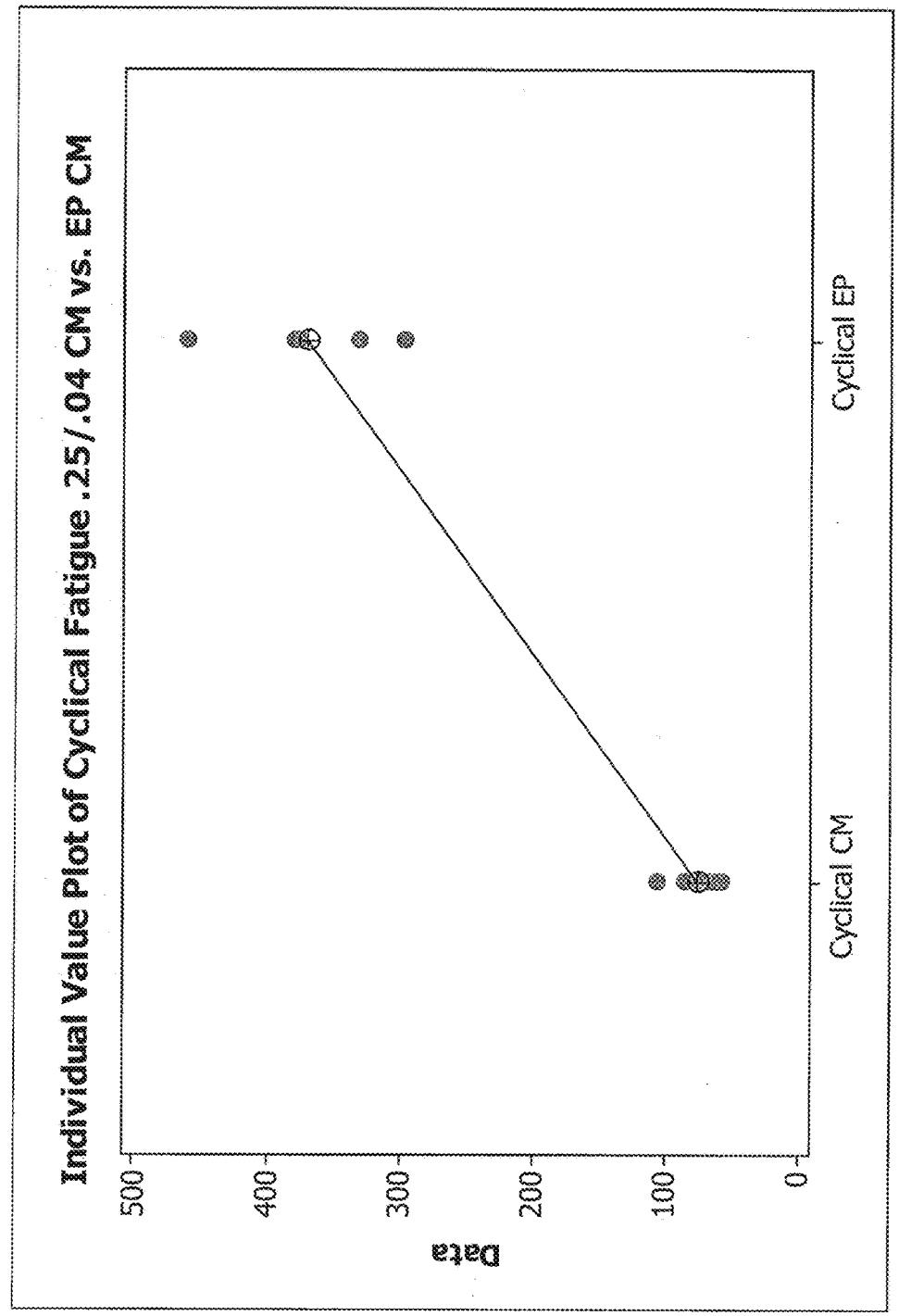
FIG. 13 shows comparative cyclical fatigue measurements including those involving heat treated instruments with no prior electropolishing step as compared to heat treated instruments that had undergone a prior electropolishing step.
Figure 14:
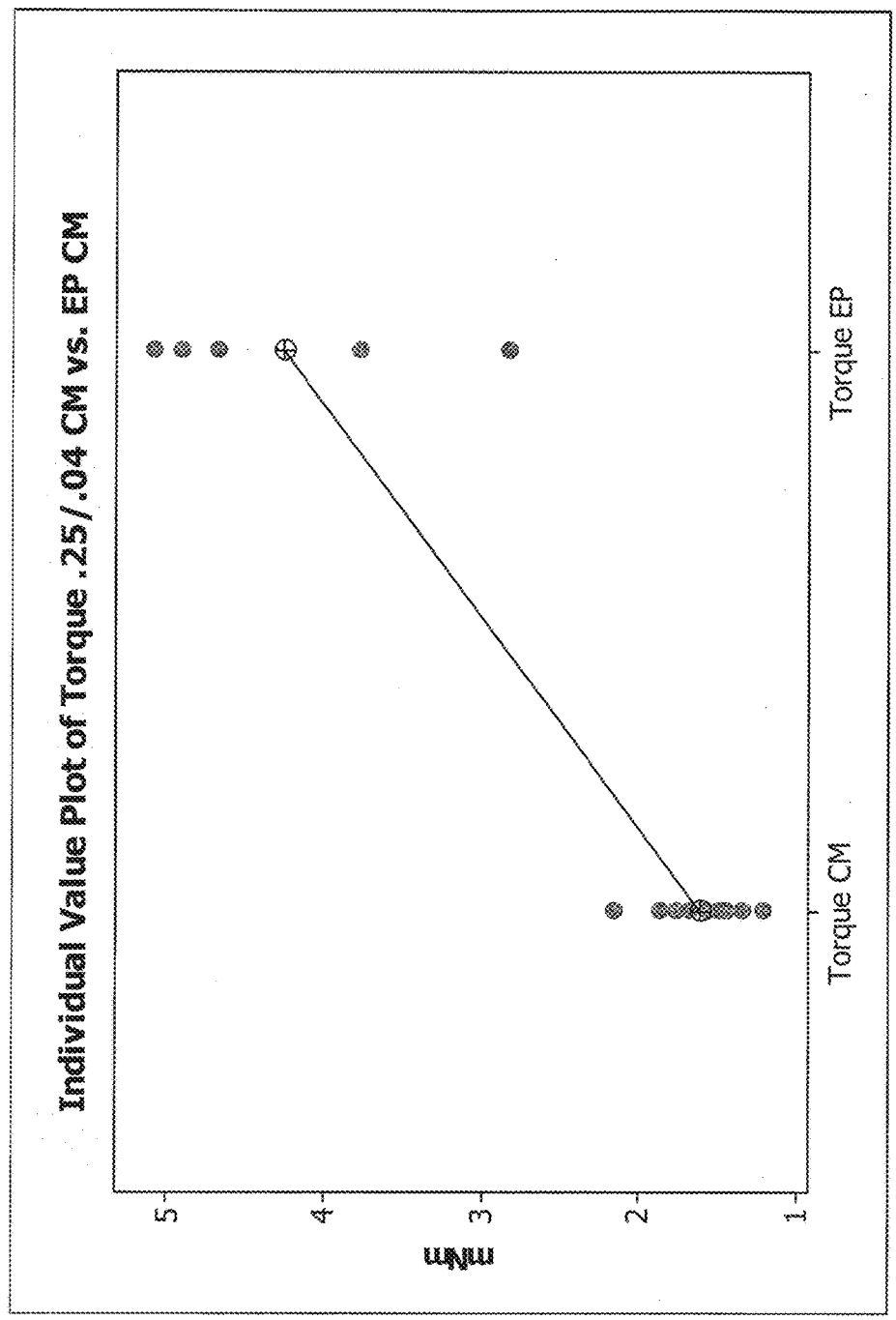
FIG. 14 shows comparative torque measurements including those involving heat treated instruments with no prior electropolishing step as compared to heat treated instruments that had undergone a prior electropolishing step.
Figure 15:
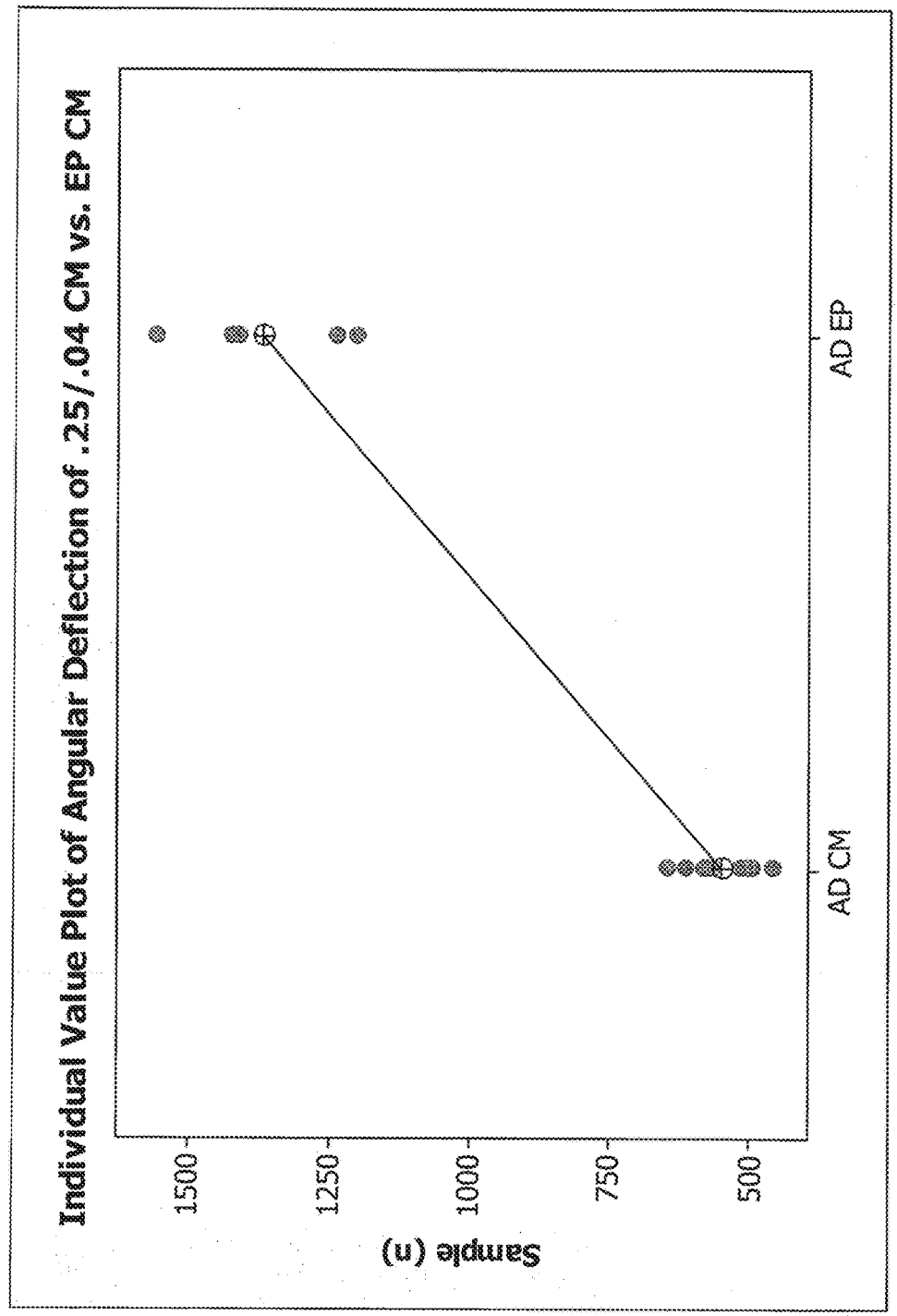
FIG. 15 shows comparative angular deflection measurements including those involving heat treated instruments with no prior electropolishing step as compared to heat treated instruments that had undergone a prior electropolishing step.

Applicants tested ten pieces of 0.25/0.04 (size/taper rate) Typhoon brand endodontic instruments in May 2010. The test results indicated substantially improved cyclical fatigue at 60° (angular), improved torque, and improved angular deflection when compared to similarly heat treated endodontic instruments that were not electropolished prior to heat treatment. The results are summarized below in Table 5, and graphically shown in FIGS. 13-15 wherein FIG. 13 shows the comparative cyclical fatigue measurements, FIG. 14 shows the comparative torque measurements, and FIG. 15 shows the comparative angular deflection measurements. The parameters used for the testing included use of a Esma Electro-polishing machine with E272 Acid wherein the temperature of the acid was kept at about 80° C. Each run lasted approximately 240 seconds and approximately 25 volts of DC power was applied through the positive and negative circuits of the electro-polishing machine.

TABLE 5

| ITEM | NAME | CRITERIA | RESULTS | | COMMENTS | | |
|---|---|---|---|---|---|---|---|
| | | | | | N | Mean | StDev | SE Mean |
| 1 | Cyclical Fatigue @ 60° | Past product group comparison | Must be greater than control group | Cyclical CM | 7 | 76.0 | 16.8 | 6.4 |
| | | | | Cyclical EP | 5 | 370.0 | 61.6 | 28 |
| 2 | Torque | Past product group comparison | Must be greater than control group | Torque CM | 9 | 1.613 | 0.288 | 0.096 |
| | | | | Torque EP | 5 | 4.261 | 0.946 | 0.42 |
| 3 | Angular Deflection | Past product group comparison | Must be greater than control group | AD CM | 10 | 549.8 | 58.3 | 18 |
| | | | | AD EP | 5 | 1370 | 146 | 65 |

Figure 16:
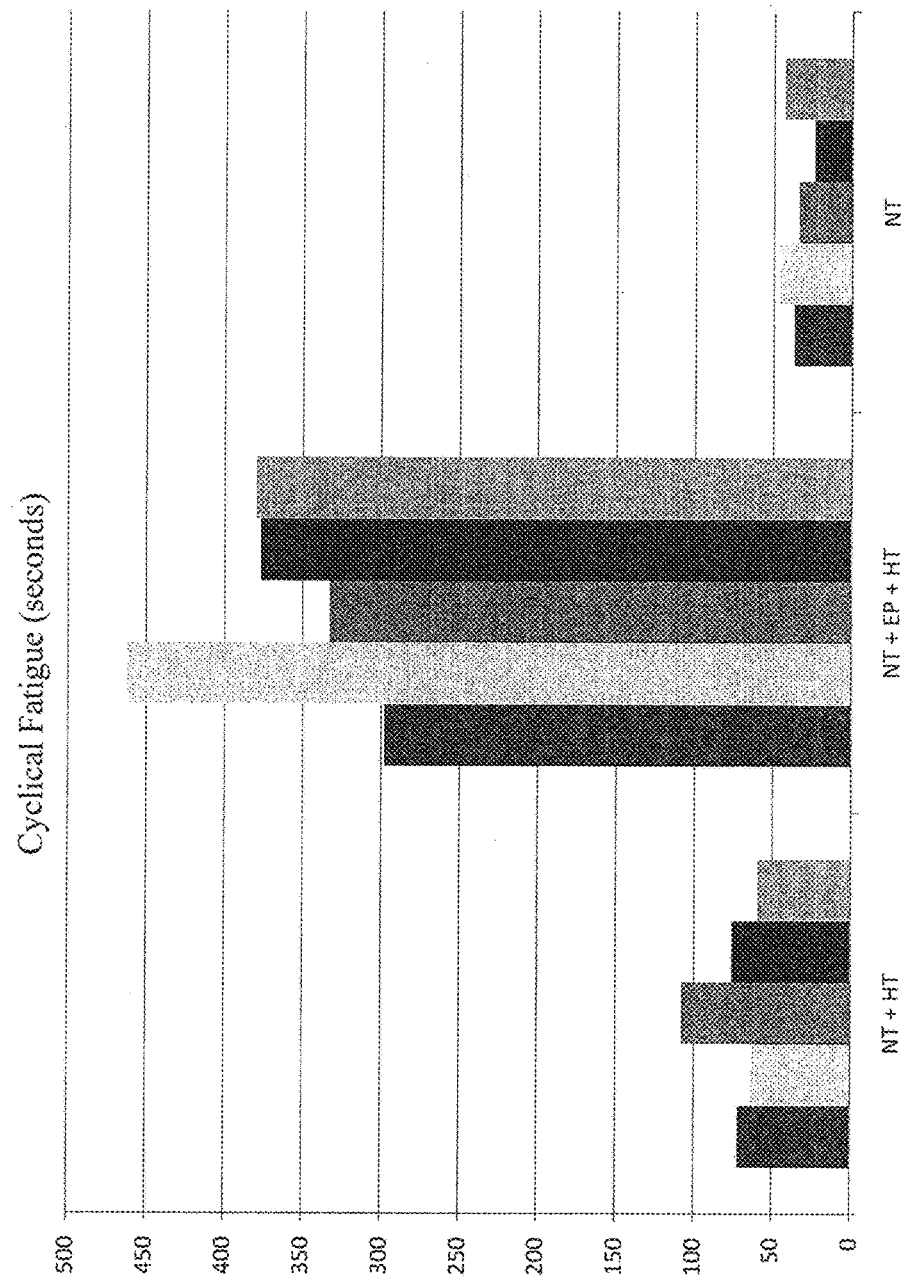
FIG. 16 shows comparative cyclical fatigue measurements including those involving nickel titanium instruments with no prior heat treatment or electropolishing step ("NT"), heat treated instruments with no prior electropolishing step ("NT+HT"), and heat treated instruments that had undergone a prior electropolishing step ("NT+HT+EP")
Figure 17:
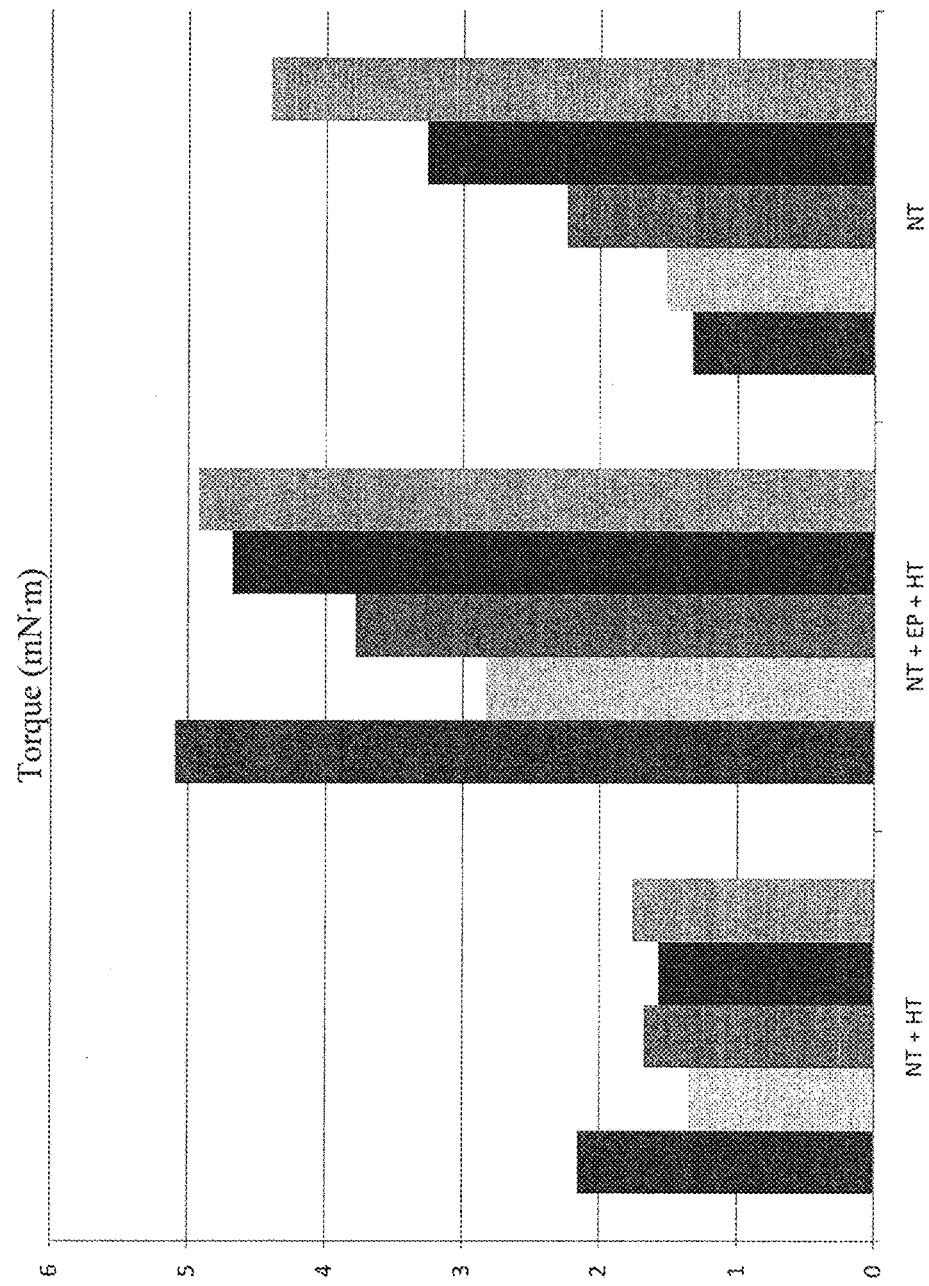
FIG. 17 shows comparative torque measurements including those involving nickel titanium instruments with no prior heat treatment or electropolishing step ("NT"), heat treated instruments with no prior electropolishing step ("NT+HT"), and heat treated instruments that had undergone a prior electropolishing step ("NT+HT+EP")
Figure 18:
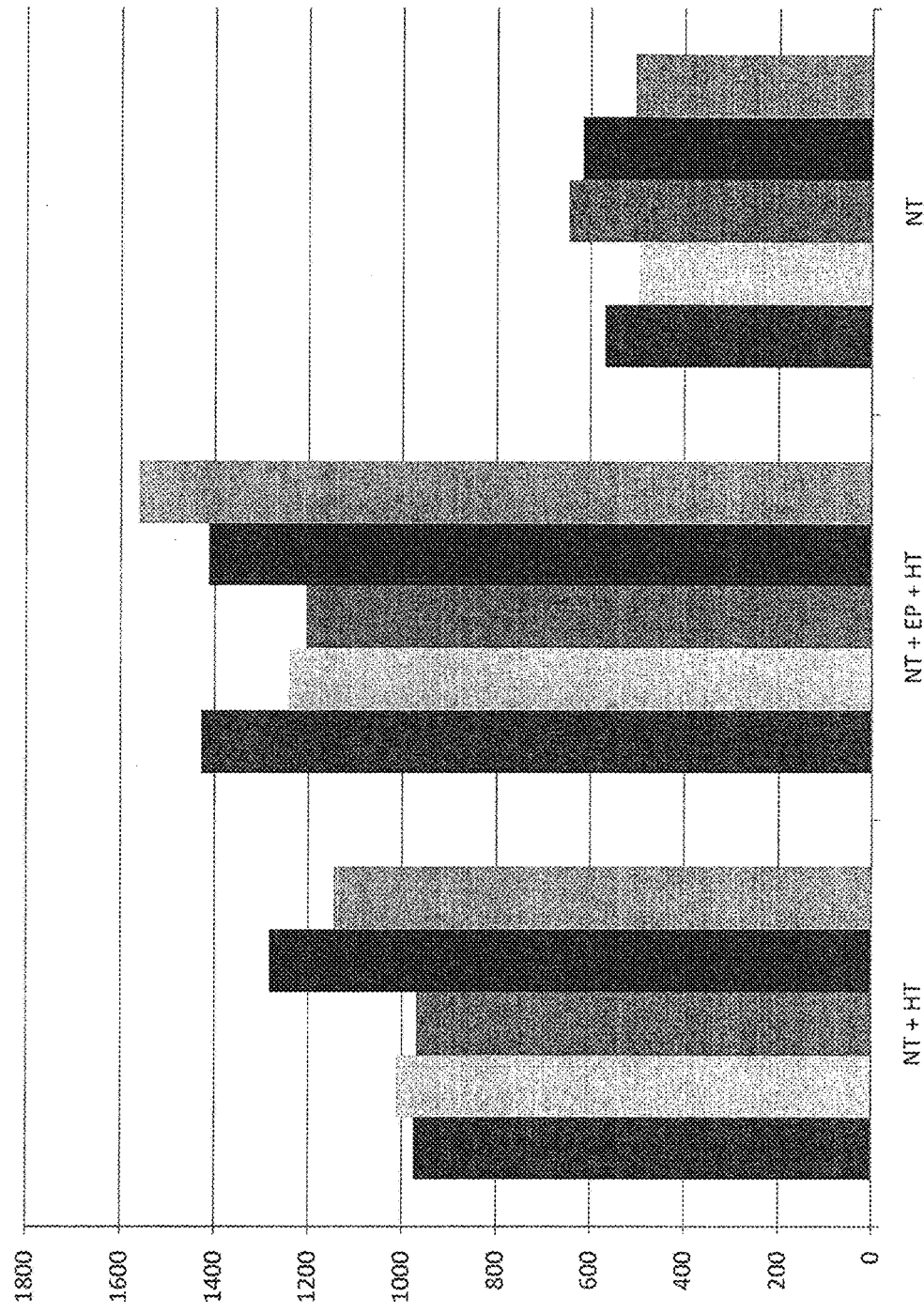
FIG. 18 shows comparative angular deflection measurements including those involving nickel titanium instruments with no prior heat treatment or electropolishing step ("NT"), heat treated instruments with no prior electropolishing step ("NT+HT"), and heat treated instruments that had undergone a prior electropolishing step ("NT+HT+EP")

Applicants further tested at least five different groups of nickel-titanium endodontic instruments wherein some had not been heat treated, some had been treated without a prior electropolishing step, some had been electropolished without a prior heat treating step, and the remainder were heat treated with a prior electropolishing step. The comparative data is shown in Table 6 below as well FIGS. 16-18 wherein FIG. 16 shows comparative cyclical fatigue, FIG. 17 shows comparative torque measurements, and FIG. 18 shows comparative angular deflection measurements.

TABLE 6

| Cyclical Fatigue | | | Torque | | | Angular Deflection | | |
|---|---|---|---|---|---|---|---|---|
| NT + HT | NT + EP + HT | NT | NT + HT | NT + EP + HT | NT | NT + HT | NT + EP + HT | NT |
| 72 | 298 | 37 | 2.158251975 | 5.09347466 | 1.329483217 | 975 | 1428 | 569 |
| 63 | 462 | 46 | 1.346749233 | 2.83162659 | 1.519409391 | 1012 | 1241 | 498 |
| 108 | 333 | 34 | 1.674803533 | 3.78125746 | 2.244582054 | 969 | 1205 | 647 |

TABLE 6-continued

| Cyclical Fatigue | | | Torque | | | Angular Deflection | | |
|---|---|---|---|---|---|---|---|---|
| NT + HT | NT + EP + HT | NT | NT + HT | NT + EP + HT | NT | NT + HT | NT + EP + HT | NT |
| 76 | 377 | 24 | 1.571207438 | 4.67909028 | 3.263276987 | 1283 | 1413 | 617 |
| 59 | 380 | 43 | 1.761133612 | 4.9208145 | 4.40283403 | 1146 | 1561 | 506 |

NT = Nickel-Titanium instrument
HT = Heat treatment step
P = Electropolishing step Based on the results shown in FIGS. 13-18, Table 5, and Table 6, this disclosure further includes a method for treating medical instruments including electropolishing a medical instrument; and placing a medical instrument into an environment held at least at about 450° C. to about 550° C., more preferably from about 475° C. to about 525° C., and most preferably from about 490° C. to about 510° C. for a period of from about 90 minutes to about 180 minutes and more preferably from about 120 minutes to about 150 minutes. The dental instrument is preferably an endodontic instrument made from at least about 50% of a superelastic alloy, and the instrument is preferably a file, reamer, or a broach. Alternatively, the medical instrument can include an orthodontic tool, wire, and/or appliance. The superelastic alloy is preferably Nickel-Titanium. The heat treated medical instrument preferably is placed in a metal pan with freedom of movement during the heating step.

Figure 21:
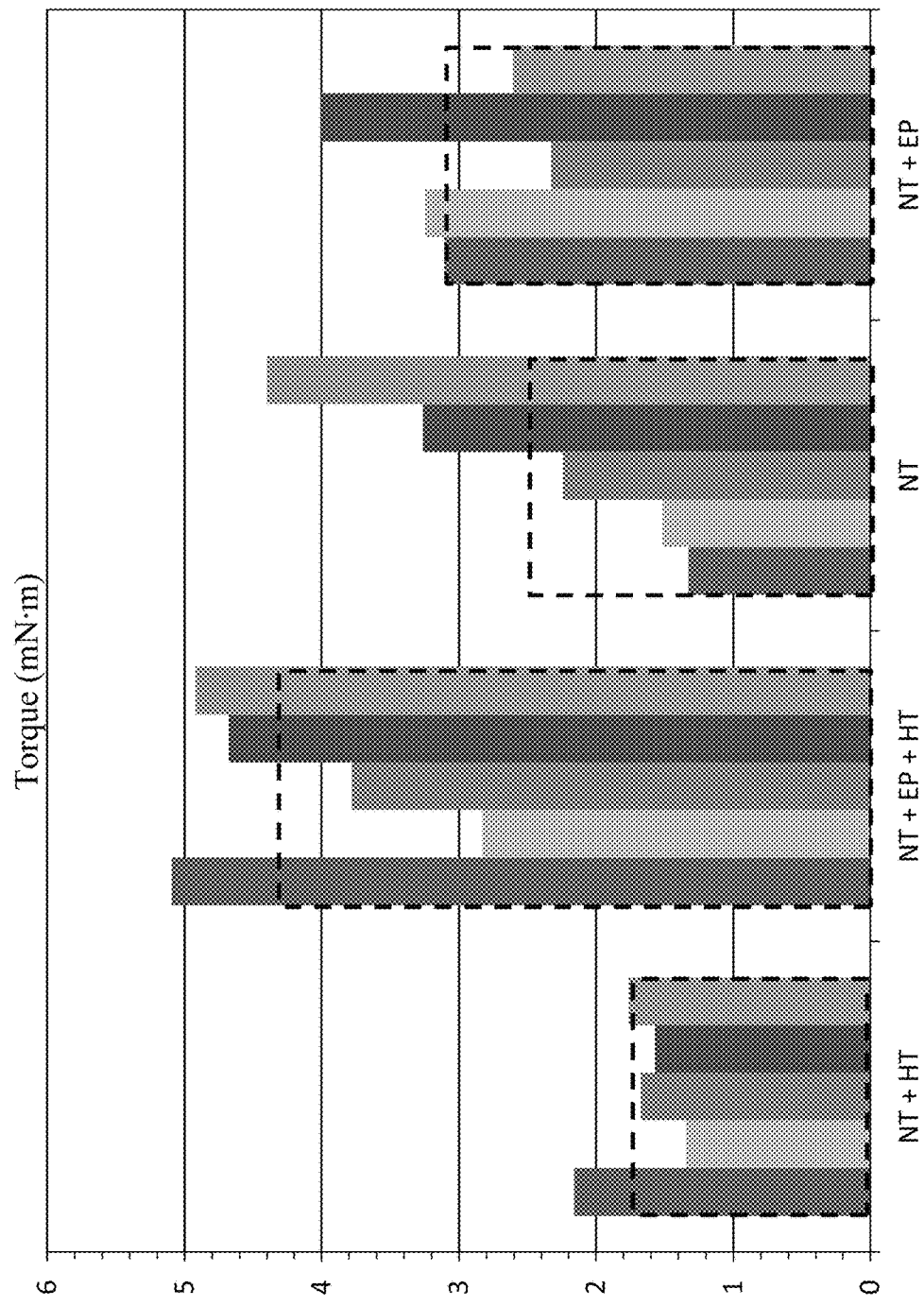
FIG. 21 shows comparative torque measurements including those involving nickel titanium instruments with no prior heat treatment or electropolishing step ("NT"), heat treated instruments with no prior electropolishing step ("NT+HT"), heat treated instruments that had undergone a prior electropolishing step ("NT+HT+EP"), and electropolished instruments with no prior heat treatment step (NT+EP), and the respective average values of these categories shown by the large dashed rectangular bars around each respective group of smaller bars.

FIG. 20 shows the average relative improvements in cyclical fatigue, torque, and angular deflection provided by the electropolishing step alone; FIG. 21 shows the average relative improvements in cyclical fatigue, torque, and angular deflection provided by the heating step alone; and FIG. 22 shows the average relative improvements in cyclical fatigue, torque, and angular deflection wherein both a heating step and electropolishing step were performed on the same instruments.

without an electropolishing step. The dashed rectangular boxes in FIGS. 20-22 and 23A-23C represent average values and provide a clearer picture of how the electropolishing step and the heating step together provide a synergistic improving effect on all of the tested categories including cyclical fatigue, torque, and angular deflection when compared to merely heating alone or electropolishing alone.

Figure 24:
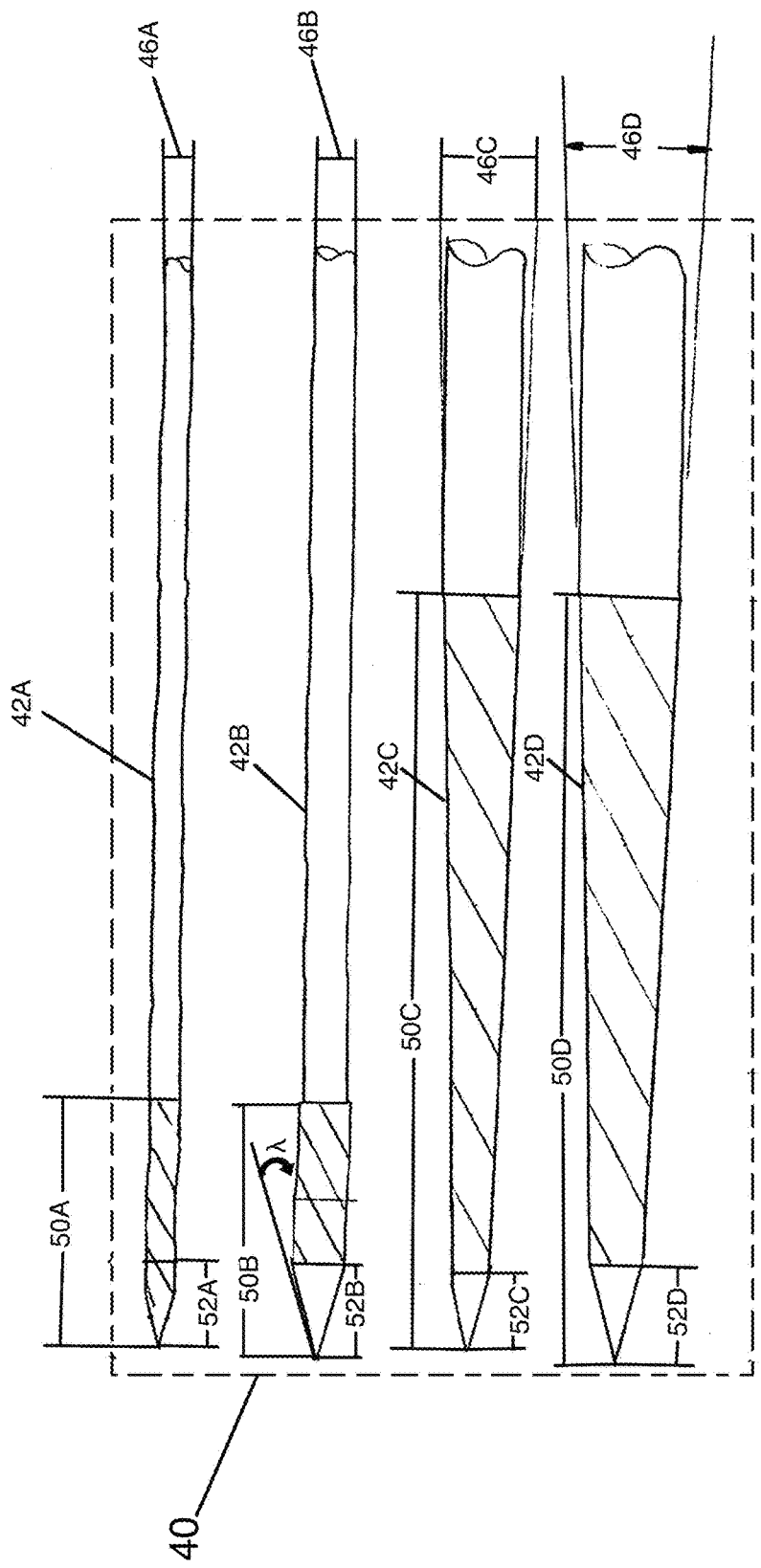
FIG. 24 shows a side view of a kit including a plurality of apex locating dental tools according to one embodiment of the present invention.

In addition to the treated medical instruments and related methods described above, another embodiment involves forming a heat treated NiTi instrument to a particular shape and returning the instruments to its original shape after the application of sufficient heat. In one example, an endodontic instrument made from a primarily superelastic alloy such as NiTi may be deformed by, for example, an endodontic surgeon to fit a particular use. One specific example includes forming a dental obturator to a particular shape for filling a root canal with sealing materials. After the endodontic instrument is used for the particular purpose, it may be heated to at least its transformation temperature at which point the instrument returns to its initial, undeformed shape. Additionally, this process of deforming and returning the instrument to its original undeformed shape may be used for other endodontic and orthodontic instruments. These steps can also be used, for example, with respect to the kit 40 including a plurality of endodontic tools 42 shown in FIG. 24.

TABLE 7

| Cyclical Fatigue | | | | Torque | | | | Angular Deflection | | | |
|---|---|---|---|---|---|---|---|---|---|---|---|
| NT + HT | NT + EP + HT | NT | NT + EP | NT + HT | NT + EP + HT | NT | NT + EP | NT + HT | NT + EP + HT | NT | NT + EP |
| 72 | 298 | 37 | 44 | 2.158252 | 5.09347466 | 1.33 | 3.107883 | 975 | 1428 | 569 | 803.87 |
| 63 | 462 | 46 | 32 | 1.346749 | 2.83162659 | 1.52 | 3.246011 | 1012 | 1241 | 498 | 724.25 |
| 108 | 333 | 34 | 37 | 1.674804 | 3.78125746 | 2.24 | 2.330912 | 969 | 1205 | 647 | 601.05 |
| 76 | 377 | 24 | 37 | 1.571207 | 4.67909028 | 3.26 | 4.005716 | 1283 | 1413 | 617 | 785.24 |
| 59 | 380 | 43 | 37 | 1.761134 | 4.9208145 | 4.4 | 2.607168 | 1146 | 1561 | 506 | 609.84 |

Figure 23C:
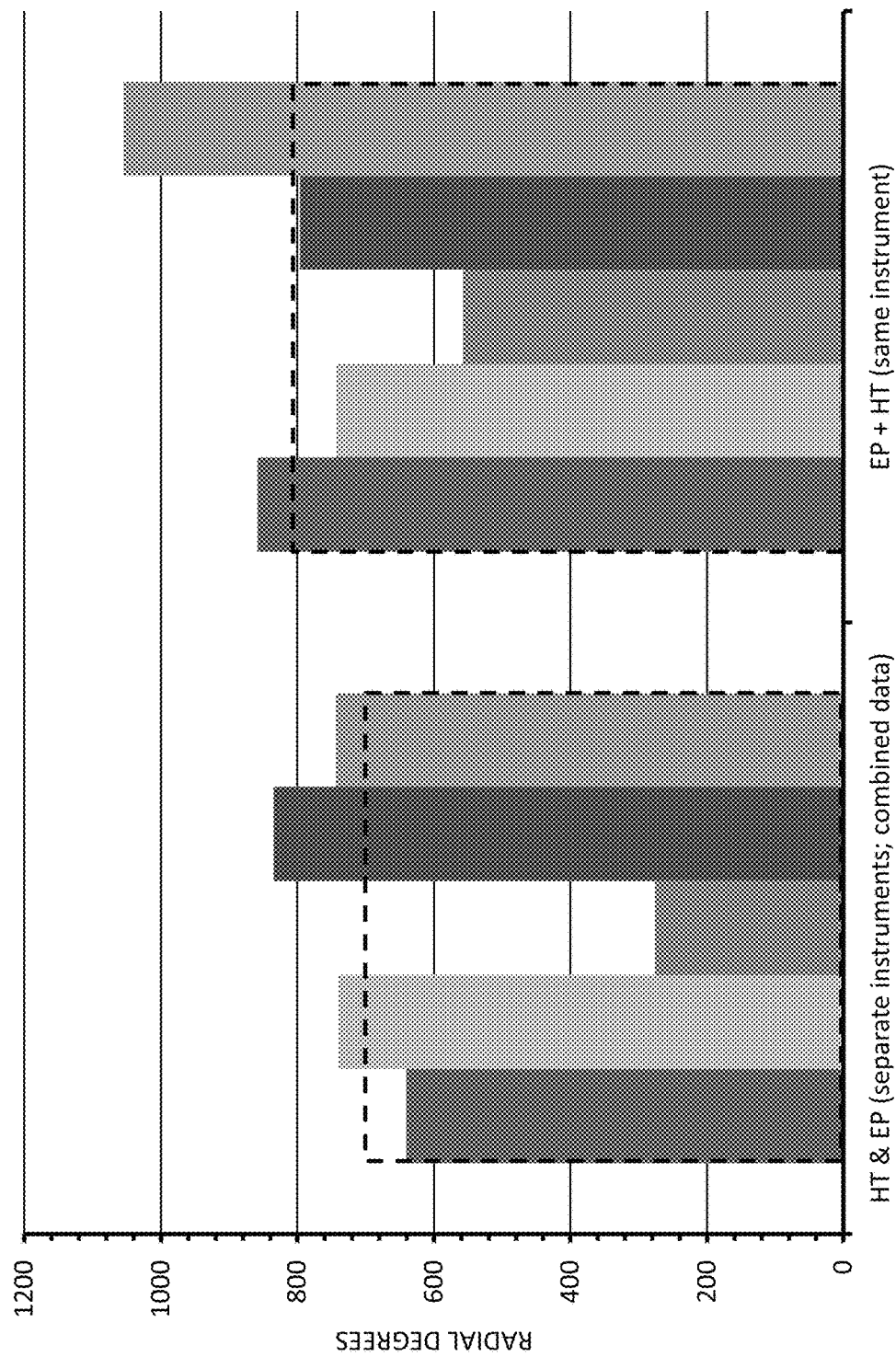
FIG. 23C shows comparative angular deflection measurements including the combined measurements of heat treated NiTi instruments with no prior electropolishing step ("HT") and electropolished instruments with no prior heat treatment step ("EP"), the sum of which are designated as "HT & EP (separate instruments; combined data)"; versus heat treated instruments that also underwent a prior electropolishing step, such instruments designated as "EP+HT (same instrument)"; the respective average values of these categories shown by the large dashed rectangular bars around each respective group of smaller bars.

NT = Nickel-Titanium instrument
HT = Heat treatment step
EP = Electropolishing step FIGS. 23A-23C show the results of the cumulative HT and EP data from FIGS. 20-22 and the net effect of separately combined HT and EP data versus the synergistic effect of treating the same instrument with both an electropolishing step and a heating step. In FIGS. 23A-23C, the baseline data for NiTi is subtracted out in each instance to more clearly show that when both heating and electropolishing steps are performed on the same instruments versus the combined data of separately treated batches of instruments wherein one batch were heat treated and the other were treated by electropolishing techniques, the instruments that underwent both electropolishing and heat treatment demonstrated notably superior results. This deviation demonstrates a synergistic effect when instruments as described herein are both heat treated and electropolished versus being heat treated The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A method for modifying a physical characteristic of an endodontic instrument made from at least about 50% by mass of a superelastic alloy, the method comprising a machining step to form a working portion of the endodontic instrument and then placing the endodontic instrument in a heated environment having a temperature of 450° C.-550° C. for over 180 minutes.

2. The method of claim 1, wherein the endodontic instrument comprises an instrument selected from the group consisting of a file, rasp, broach, obturator, plugger, and spreader.

3. The method of claim 1 wherein the heated environment comprises air.

4. The method of claim 1 further comprising the step of placing a resistance layer along a first section of the endodontic instrument prior to placing the endodontic instrument in the heated environment, wherein the resistance layer prevents the first section from undergoing the same degree of heat treatment in the heated environment as the remaining portions of the endodontic instrument that were not covered by the resistance layer.

5. The method of claim 4 wherein the first section comprises all of the endodontic instrument except for from about 6 mm to no less than 4 mm from a terminus of a tapered end of the endodontic instrument.

6. The method of claim 1 further comprising a step of electropolishing the instrument prior to placing the instrument in the heated environment.

7. The method of claim 1 further comprising the step of cooling the heated instrument using natural heat transfer mechanisms in ambient air.

* * * * *